(12) United States Patent
Daniel et al.

(10) Patent No.: US 6,248,327 B1
(45) Date of Patent: Jun. 19, 2001

(54) MODULATION OF ENDOTHELIAL CELL SURFACE RECEPTOR ACTIVITY IN THE REGULATION OF ANGIOGENESIS

(75) Inventors: Thomas O. Daniel; Takamune Takahashi, both of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/152,160

(22) Filed: Sep. 11, 1998

(51) Int. Cl.[7] .................. A61K 39/395; A61K 38/00; A01N 31/00; C12P 21/08
(52) U.S. Cl. .................. 424/143.1; 424/152.1; 424/156.1; 514/2; 514/12; 514/21; 530/388.22; 530/388.85
(58) Field of Search .................. 424/143.1, 152.1, 424/156.1; 514/2, 12, 21; 530/388.22, 388.85

(56) References Cited

U.S. PATENT DOCUMENTS

| | | | |
|---|---|---|---|
| 5,595,911 | 1/1997 | Tonks . | |
| 5,660,827 | 8/1997 | Thorpe et al. | 424/152.1 |
| 5,733,876 | 3/1998 | O'Reilly et al. | 514/12 |
| 5,753,230 | 5/1998 | Brooks et al. | 424/158.1 |
| 5,762,918 | 6/1998 | Thorpe | 424/78.17 |
| 5,766,591 | 6/1998 | Brooks et al. | 424/184.1 |
| 5,776,427 | 7/1998 | Thorpe et al. | 424/1.49 |
| 5,863,781 | 1/1999 | Tonks . | |

FOREIGN PATENT DOCUMENTS

| | | |
|---|---|---|
| 0520029 | 5/1995 | (EP) . |
| WO91/13989 | 9/1991 | (WO) . |
| WO95/30008 | 11/1995 | (WO) . |
| WO98/04712 | 2/1998 | (WO) . |
| WO99/02704 | 1/1999 | (WO) . |

OTHER PUBLICATIONS

Honda et al., "Molecular Cloning, Characterization, and Chromosomal Localization of a Novel Protein–Tyrosine Phosphatase, HPTPη", *Blood*, vol. 84, (1995) pp. 4186–4194.

Borges et al., "Cloning and Characterization of Rat Density–Enhanced Phosphatase–1, a Protein Tyrosine Phosphatase Expressed by Vascular Cells", *Circulation Research*, vol. 79, No. 3, (Sep. 1996) pp. 570–580.

Keane et al., "The Protein Tyrosine Phosphatase DEP–1 is Induced During Differentiation and Inhibits Growth of Breast Cancer Cells", *Cancer Research*, vol. 56, (Sep. 15, 1996), pp. 4236–4243.

Östman et al., "Expression of DEP–1, a Receptor–Like Protein–Tyrosine–Phosphatase, is Enhanced with Increasing Cell Density", *Proc. Natl. Acad. Sci. USA*, vol. 91, (Oct. 1994), pp. 9680–9684.

PCT International Search Report for WO 98/04712.

*Primary Examiner*—Geetha P. Bansal
(74) *Attorney, Agent, or Firm*—Jenkins & Wilson, P.A.

(57) ABSTRACT

A method of modulating angiogenesis in a vertebrate subject, the method comprising administering to the vertebrate subject an ECRTP/DEP-1 receptor activity-modulating amount of a composition, whereby an ECRTP/DEP-1 receptor within the vertebrate subject is contacted by the composition; and modulating angiogenesis through the contacting of the ECRTP/DEP-1 receptor with the composition. Optionally, the composition includes a monoclonal antibody which preferentially binds the ECRTP/DEP-1 receptor.

22 Claims, 12 Drawing Sheets

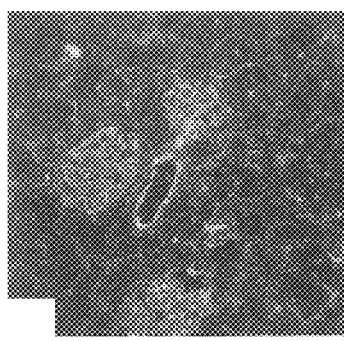 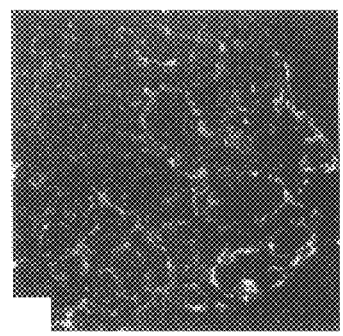 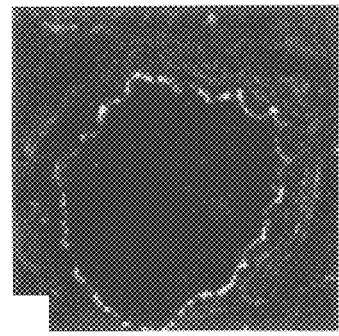
FIG. 2A    FIG. 2B    FIG. 2C
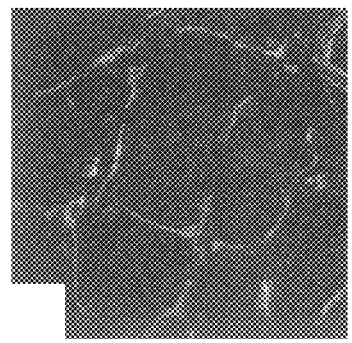 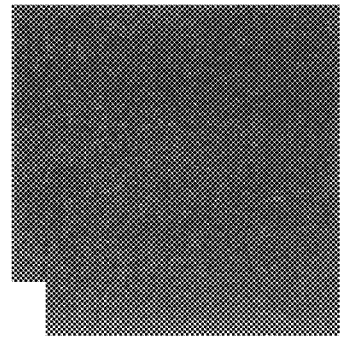
FIG. 2D    FIG. 2E Artery Glomerulus

MODULATION OF ENDOTHELIAL CELL SURFACE RECEPTOR ACTIVITY IN THE REGULATION OF ANGIOGENESIS

GRANT STATEMENT

This work was supported by NIH grants DK38517 and CA 68485. The U.S. Government has certain rights in the invention.

TECHNICAL FIELD

The present invention relates generally to the modulation of the activity of an endothelial cell surface receptor in the regulation of endothelial cell proliferation and migration and in the regulation of angiogenesis. More particularly, the present invention relates to the modulation of ECRTP/DEP-1 receptor activity in the regulation of endothelial cell proliferation and migration and in the regulation of angiogenesis.

BACKGROUND OF THE INVENTION

As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels. The term "endothelial modulating activity" means the capability of a molecule to modulate angiogenesis in general and, for example, to stimulate or inhibit the growth of endothelial cells in culture. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, and abnormal growth by endothelial cells and supports the pathological damage seen in these conditions. The diverse pathological disease states in which unregulated angiogenesis is present have been grouped together as angiogenic dependent or angiogenic associated diseases.

It is also recognized that angiogenesis plays a major role in the metastasis of a cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

The development of renal glomerular capillaries is anatomically segregated and temporally staged in a multi-step process. The process involves recruitment of endothelial progenitors from adjacent mesenchyme, assembly of an arborized branching network, and maturation and specialization of endothelial cells adjacent to mesangial and visceral epithelial cells. Receptors for extracellular matrix components, cell surface molecules and growth factors have been assigned roles to mediate steps in this assembly process. See e.g., Wallner et al., *Microsc Res Tech* 39:261–284 (1997); Takahashi et al., *Kidney Int* 53:826–835 (1998).

Vascular endothelial growth factor (VEGF) is an important participant, as it is induced in S stage developing glomerular epithelial cells, and endothelial progenitors that are recruited to glomerular capillaries from the adjacent metanephric mesenchyme express the VEGF receptor, flk-1. Robert et al., *Am J Physiol* 271:F744–F753 (1996).

Neutralizing VEGF antibodies interrupt postnatal murine glomerular capillary development. Kitamoto et al., *J Clin Invest* 99:2351–2357 (1997). Deletion of either PDGFβ receptor or PDGFβ genes in mice causes defective recruitment of mesangial cell precursors with failure of glomerular development. Soriano, P., *Genes Dev* 8:1888–1896 (1994); Leveen et al., *Genes Dev* 8:1875–1887 (1994). TGFβ1 expression and type II TGFβ receptors appear critical for vascular development in the embryonic yolk sac (prior to renal development), and type II receptors mediate in vitro capillary morphogenesis of endothelial cells derived from bovine glomeruli. Choime et al., *J Biol Chem* 270:21144–21150 (1995).

Early evidence suggests that Eph family receptors and their ephrin ligands participate in glomerular vascular development. EphB1 receptors are expressed in isolated mesenchymal cells in a pattern similar to that of flk-1, and high level expression of ephrin-B1 is seen at the vascular cleft of developing glomeruli, as well as in capillary endothelial cells of mature glomeruli. Daniel et al., *Kidney Int* 50:S-73-S-81 (1996). Oligomerized forms of ephrin-B1 stimulate in vitro assembly of human renal microvascular endothelial cells (HRMEC) into capillary-like structures. Stein et al., *Genes Dev* 12:667–678 (1998).

A selected subclass of receptor tyrosine phosphatases, including DPTP10D, serve important roles in directing axonal migration and neural network assembly. Desai et al., *Cell* 84:599–609 (1996). Recent data has identified mRNA expression of a related receptor phosphatase, ECRTP/DEP-1, in arterial sites in mammalian kidney. Borges et al., *Circulation Research* 79:570–580 (1996). To date, however, there has been no evidence to implicate receptor tyrosine phosphatases in microvascular or glomerular capillary assembly or maturation.

Vascular endothelial cells display a diverse range of vascular bed specific properties (Gumkowski et al., *Blood Vessels* 24:11–13 (1987)), yet the requirement to maintain a continuous, antithrombotic monolayer lining the vascular space imposes rigorous requirements that their proliferation, migration and differentiation be regulated by interendothelial contacts. Specialized intercellular contacts permit communication among interacting endothelial cells (Lampugnani et al., *J Cell Biol* 129:203–217 (1995)) yet the mechanisms regulating arrest of proliferation and migration in response to interendothelial contact have not been elucidated. Tight regulatory control over proliferation imposed by interendothelial cell contact is apparent in the low basal mitotic index among endothelial cells in existing vessels. Engerman et al., *Laboratory Investigation* 17:738–744 (1967). This is in contrast with the proliferative endothelial responses that are evoked by mechanical disruption of large vessels. More et al., *J Patho* 172:287–292 (1994). Similar proliferation and migration responses are stimulated at the margin of a confluent endothelial monolayer by "wounding", or physical removal cells from the packed monolayer. Coomber, *J Cell Biochem* 52:289–296 (1993).

The molecular basis for effects of interendothelial contact on migratory and proliferative responses is not defined, yet studies of cultured cells have shown that endothelial, fibroblast, and epithelial cells grow to confluency at a predictable density, then arrest proliferation (density arrest). Augenlicht and Baserga, *Exp Cell Res* 89:255–262 (1974); Beekhuizen and van Furth, *J Vascular Res* 31:230–239 (1994); Rijksen et al., *J Cell Physiol* 154:393–401 (1993). This phenomenon may be very relevant to the behavior of endothelial cells in vascular sites in situ. Indeed, model culture systems of endothelial "wounding" have shown that endothelial cells at the edge of an imposed "wound" rapidly extend lamellae, spread, migrate and proliferate to replace the deficit created by mechanical disruption of the monolayer. Coomber, *J Cell Biochem* 52:289–296 (1993).

Pallen and Tong observed that membrane-associated tyrosine phosphatase activity recovered from cultured Swiss 3T3 cells increased eight (8)-fold (expressed as activity/mg protein) as cells approached a density of $5 \times 10^4/cm^2$, while soluble fraction tyrosine phosphatase was unaffected by cell density. Pallen and Tong, *Proc Natl Acad Sci USA* 88:6996–7000 (1991). Ostman et al. determined that the abundance of a receptor tyrosine phosphatase cloned from HeLa cells and named DEP-1, is increased as cells approach high density. Ostman et al., *Proc Natl Acad Sci USA* 91:9680–9684 (1994). However, no links between molecules that evoke proliferation arrest and receptor tyrosine phosphatases have been made.

To date, available information does not indicate what sort of receptor-ligand interaction may mediate a cell surface generated signal for density or contact arrest. The identification of such a receptor-ligand interaction is therefore needed in that it will serve as a basis for intervention in a disorder wherein density or contact arrest, or the preclusion of density or contact arrest, has therapeutic value. Such disorders include disorders characterized by undesired angiogenesis, such as angiogenesis associated with tumor growth. Thus, what is also needed is a composition and method which can inhibit the unwanted growth of blood vessels, especially into tumors. The composition and method should attenuate the formation of the capillaries in the tumors thereby inhibiting the growth of the tumors.

SUMMARY OF THE INVENTION

In accordance with the present invention, a method of modulating angiogenesis in a vertebrate subject is provided. The method comprises administering to the vertebrate subject an ECRTP/DEP-1 receptor activity modulating amount of a composition, whereby an ECRTP/DEP-1 receptor within the vertebrate subject is contacted by the composition; and modulating angiogenesis through the contacting of the ECRTP/DEP-1 receptor with the composition.

In accordance with the present invention a method of modulating endothelial cell migration and proliferation in a vertebrate subject is also provided. The method comprises administering to the vertebrate subject an ECRTP/DEP-1 receptor activity-modulating amount of a composition, whereby an ECRTP/DEP-1 receptor within the vertebrate subject is contacted by the composition; and modulating endothelial cell migration and proliferation through the contacting of the ECRTP/DEP-1 receptor with the composition.

In accordance with the present invention there is also provided an antibody which preferentially binds the ECRTP/DEP-1 receptor. Optionally, the antibody comprises a monoclonal antibody or fragment or derivative thereof which preferentially binds the ECRTP/DEP-1 receptor.

In accordance with the present invention, a method for isolating an endogenous ligand for an ECRTP/DEP-1 receptor is also provided. The method comprises the steps of contacting cells or cell lysates having the ligand with ECRTP/DEP-1 receptor; and isolating the ligand which binds with ECRTP/DEP-1 receptor.

In accordance with the present invention there are also provided methods for performing a screening assay for identifying a compound that modulates an activity of an ECRTP/DEP-1 receptor in both a cell-based and a cell-free assay. In a cell-based assay, the method comprises the steps of establishing replicate test and control cultures of cells that express the ECRTP/DEP-1 receptor; administering a candidate compound to the cells in the test culture but not the control culture; measuring ECRTP/DEP-1 receptor activity in cells in the test and the control cultures; and determining that the candidate compound modulates the ECRTP/DEP-1 receptor activity in a cell if the ECRTP/DEP-1 receptor activity measured for the test culture is greater or less than the ECRTP/DEP-1 receptor activity measured for the control culture.

In a cell-free system, the method comprises the steps of establishing a control system comprising an ECRTP/DEP-1 receptor and a ligand wherein the ECRTP/DEP-1 receptor is capable of binding to the ligand; establishing a test system comprising the ECRTP/DEP-1 receptor, the ligand, and a candidate compound; measuring the binding affinity of the ECRTP/DEP-1 receptor and the ligand in the control and the test systems; and determining that the candidate compound modulates ECRTP/DEP-1 receptor activity in a cell-free system if the binding affinity measured for the test system is less than or greater than the binding affinity measured for the control system.

In accordance with the present invention there is also provided a method for delivering a therapeutic composition to a tissue in a patient, wherein the tissue is characterized as having undesirable endothelial cell proliferation. The method comprises the steps of introducing into the patient a biologically effective amount of an antibody operatively linked to a selected therapeutic agent, the antibody preferentially binding to an ECRTP/DEP-1 receptor on the surface of the endothelial cells, whereby an ECRTP/DEP-1 receptor within the vertebrate subject is contacted by the antibody; and delivering the therapeutic composition to the tissue through the contacting of the ECRTP/DEP-1 receptor with the composition.

It is therefore an object of the present invention to localize and characterize a receptor-ligand interaction which mediates a cell surface-generated signal for density or contact arrest.

It is another object of the present invention to provide for the modulation of a cell surface receptor activity in endothelial cells to mediate a cell surface-generated signal for density or contact arrest.

It is still another object of the present invention to provide for the modulation of a cell surface receptor activity for use in the inhibition or stimulation of angiogenesis.

It is yet another object of the present invention to identify compounds which modulate a receptor-ligand interaction which mediates a cell surface-generated signal for density or contact arrest.

Some of the aspects and objects of the invention having been stated hereinabove, other aspects and objects will become evident as the description proceeds, when taken in connection with the accompanying drawings as best described hereinbelow.

BRIEF DESCRIPTION OF THE DRAWINGS

FIG. 1 depicts recognition by antibodies ECRTPAb-1 & ECRTPAb-2 of recombinant and over-expressed ECRTP/DEP-1 receptor.

FIG. 2 is a series of photographs depicting the abundance of ECRTP/DEP-1 receptor in endothelial cells of adult human kidney. Acetone fixed frozen sections (5 μm thickness) of human kidney were incubated with ECRTPAb-1 (panels A–D) or a class matched control monoclonal antibody (panel E) and bound antibody was detected by epifluorescence microscopy, as described in Methods. ECRTPAb-1 prominently labeled glomerular, peritubular and arterial endothelial cells. Magnifications were A)×100; B)×600; C)×600; D×400; and E)×100.

FIG. 5 depicts distribution of ECRTP/DEP-1 receptor of inter-endothelial contacts in cultured human endothelial cells, but ECRTP/DEP-1 receptor does not dissociate from junctions with VE cadherin.

FIG. 6 shows that endothelial cell density imposes growth arrest and increases lectin recoverable tyrosine phosphatase activity.

FIG. 8 shows that ECRTP/DEP-1 receptor overexpression, or bivalent antibody against ECRTP/DEP-1, ECRTPAb-1, imposes proliferation arrest on HRMEC.

FIG. 9 depicts inhibition of endothelial migration by ECRTPAb-1.

DETAILED DESCRIPTION OF THE INVENTION

Figure 1A:
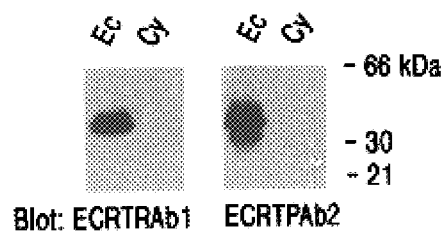
FIG. 1A is an autoradiograph depicting recombinant proteins representing extracellular (Ec) or cytoplasmic (Cy) domains of ECRTP/DEP-1 receptor were expressed in bacteria and purified. Proteins (100 ng) were separated on a 15% SDS-polyacrylamide gels, transferred to PVDF membrane and probed with monoclonal antibodies ECRTPAb-1 or ECRTPAb-2, as indicated.

A mammalian transmembrane protein gene product called DEP-1 (for density enhanced phosphatase), ECRTP, HPTPη, CD148, BYP, depending upon species and cDNA origin), was initially cloned from fibroblasts and was subsequently shown to be expressed (hereinafter referred to as an "ECRTP/DEP-1 receptor") on all hematopoietic lineages (de la Fuente-Garcia et al., Blood 91:2800–2809 (1998), including erythroid progenitor cells, megakaryocytes and platelets, lymphocytes, polymorphononuclear leukocytes and platelets, and very prominently in endothelial cells. Borges et al., Circulation Research 79:570–580 (1996), Schoecklmann et al., J Am Soc Nephrol 5:730 (1994) (abstract). This gene product has been shown to promote differentiation of erythroid progentior cells (Kumet et al., J Biol Chem 271:30916–30921 (1996)), to modulate lymphocyte function when crosslinked with other signaling proteins (de la Fuente-Garcia et al., Blood 91:2800–2809 (1998)); and to inhibit clonal expression of breast cancer cell lines overexpressing the protein (Keane et al., Cancer Research 56:4236–4243 (1996)).

In accordance with the present invention, it has been demonstrated that antibodies specific for ectodomain epitopes of the ECRTP/DEP-1 receptor block endothelial migration and proliferation in response to phorbol myristate acetate and fetal bovine serum respectively. It is recognized that the biological activity to inhibit endothelial proliferation and migration is a strong indicator of angiogenesis inhibitory activity. Accordingly, the ECRTP/DEP-1 receptor is also a mediator of inhibitory signals that block angiogenesis.

In accordance with the present invention, then, antibodies that aggregate the ECRTP/DEP-1 receptor, including monoclonal antibody ECRTPAb-1 described herein, inhibit angiogenesis. Indeed, monoclonal antibodies against the ectodomain of ECRTP/DEP-1 receptor inhibit proliferation (as demonstrated by BrdU uptake experiments) and migration of endothelial cells. Fab fragments of the same monoclonal have no such activity. Accordingly, such monoclonal ECRTP/DEP-1 receptor antibodies described herein and derivatives thereof, have biological activity as angiogenesis inhibitors.

An endogenous ligand for the receptor ectodomain signals endothelial growth arrest. Therefore, in accordance with the present invention, a method of screening for the endogenous ligand is provided. For example, the endogenous ligand is isolated through the preparation of fusion proteins of the ECRTP/DEP-1 receptor ectodomain as affinity reagents to identify, establish assays for, and clone the putative natural ligand expressed on endothelial cells. The purified and isolated endogenous ligand thus also has therapeutic application as an angiogenesis inhibitor.

In accordance with the present invention, synthetic peptides and peptidomimetics may also be used to contact the ECRTP/DEP-1 receptor to agonise ECRTP/DEP-1 receptor activity.

The ECRTP/DEP-1 receptor is expressed on the luminal and interendothelial membranes of endothelial cells in microvascular and large arterial vessels of kidney and other organs, including but not limited to heart, spleen, muscle and skin. The ECRTP/DEP-1 receptor localizes to interendothelial contacts in cultured endothelial cells, and in regions that overlap, but localization is not limited to the VE cadherin rich junctional complexes. ECRTP/DEP-1 receptor activity (tyrosine phosphatase activity) increases approximately two times in confluent cells anticipating density mediated growth arrest. Moreover, over-expression of ECRTP/DEP-1 receptor confers growth arrest on subconfluent endothelial cells. Thus, in accordance with the present invention, a method of modulating ECRTP/DEP-1 receptor activity by contacting an ECRTP/DEP-1 receptor with an ECRTP/DEP-1 receptor modulating composition is contemplated. A method of screening for such a composition is also contemplated. Finally, a method of targeting a therapeutic composition to interendothelial contacts by preparing an antibody which preferably binds the ECRTP/DEP-1 receptor and which is bound to the therapeutic composition is also contemplated to be within the scope of the present invention.

A. General Considerations

The present invention relates generally to the discovery that angiogenesis is mediated by the ECRTP/DEP-1 receptor and that activation of ECRTP/DEP-1 receptor function inhibits angiogenesis. This discovery is important because of the role that angiogenesis plays in a variety of disease processes. By modulating angiogenesis, one can intervene in the disease, ameliorate the symptoms, and in some cases cure the disease.

Where the growth of new blood vessels is the cause of, or contributes to, the pathology associated with a disease, inhibition of angiogenesis will reduce the deleterious effects of the disease. Examples include rheumatoid arthritis, diabetic retinopathy, and the like. Where the growth of new blood vessels is required to support growth of a deleterious tissue, inhibition of angiogenesis will reduce the blood supply to the tissue and thereby contribute to reduction in tissue mass based on blood supply requirements. Examples include growth of tumors where neovascularization is a continual requirement in order that the tumor grow beyond a few millimeters in thickness, and for the establishment of solid tumor metastases.

The methods of the present invention are effective in part because the therapy is highly selective for angiogenesis and not other biological processes. As shown in the Examples, the ECRTP/DEP-1 receptor localizes to endothelial cells and thus, primarily new vessel growth contains substantial ECRTP/DEP-1 receptor, and therefore the therapeutic methods do not adversely effect mature vessels. Furthermore, the ECRTP/DEP-1 receptor is not widely distributed in normal tissues, but rather is found selectively on the surface of endothelial cells, thereby assuring that the therapy can be selectively targeted.

The discovery that binding the ECRTP/DEP-1 receptor will effectively inhibit angiogenesis allows for the development of therapeutic compositions with potentially high specificity, and therefore relatively low toxicity. Thus although the invention discloses the preferred use of an anti-ECRTP/DEP-1 receptor monoclonal antibody, one can design reagents which selectively bind ECRTP/DEP-1 receptor, and therefore do not have the side effect of modulating other biological processes other that those mediated by an ECRTP/DEP-1 receptor.

As shown by the present teachings, it is possible to prepare monoclonal antibodies highly selective for immunoreaction with the ECRTP/DEP-1 receptor that are similarly selective for modulation of ECRTP/DEP-1 receptor function. In addition, peptides can be designed to be selective for binding to an ECRTP/DEP-1 receptor, as described further herein. Prior to the discoveries of the present invention, it was not known that angiogenesis could be inhibited in vivo by the use of reagents that agonise the biological function of an ECRTP/DEP-1 receptor or other receptor tyrosine phosphatase.

Other related methods are described in U.S. Pat. Nos. 5,753,230; 5,733,876; 5,762,918; 5,776,427; 5,766,591; and 5,660,827, the entire contents of each of which are herein incorporated by reference.

Following long-standing patent law convention, the terms "a" and "an" mean "one or more" when used in this application, including the claims.

B. Methods For Inhibition of Angiogenesis

The invention provides for a method for the inhibition of angiogenesis in a tissue, and thereby modulating events in the tissue which depend upon angiogenesis. Generally, the method comprises administering to the tissue a composition comprising an angiogenesis-modulating amount of an ECRTP/DEP-1 receptor modulator.

Angiogenesis includes a variety of processes involving neovascularization of a tissue including "sprouting", vasculogenesis, or vessel enlargement, all of which angiogenesis processes are mediated by and dependent upon the expression of ECRTP/DEP-1 receptor. With the exception of traumatic wound healing, corpus luteum formation and embryogenesis, it is believed that the majority of angiogenesis processes are associated with disease processes.

There are a variety of diseases in which angiogenesis is believed to be important, referred to as angiogenic diseases, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, capillary proliferation in atherosclerotic plaques and osteoporosis, and cancer associated disorders, such as solid tumors, solid tumor metastases, angiofibromas, retrolental fibroplasia, hemangiomas, Karposi's sarcoma and the like cancers which require neovascularization to support tumor growth.

Thus, methods which inhibit angiogenesis in a diseased tissue ameliorates symptoms of the disease and, depending upon the disease, can contribute to cure of the disease. In one embodiment, the invention contemplates inhibition of angiogenesis, per se, in a tissue. The extent of angiogenesis in a tissue, and therefore the extent of inhibition achieved by the present methods, can be evaluated by a variety of methods, such as are described in the Examples for detecting an ECRTP/DEP-1-immunopositive immature and nascent vessel structures by immunohistochemistry.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

Thus, in one related embodiment, a tissue to be treated is an inflamed tissue and the angiogenesis to be inhibited is inflamed tissue angiogenesis where there is neovascularization of inflamed tissue. In this class the method contemplates inhibition of angiogenesis in arthritic tissues, such as in a patient with chronic articular rheumatism, in immune or non-immune inflamed tissues, in psoriatic tissue and the like.

The patient treated in the present invention in its many embodiments is desirably a human patient, although it is to be understood that the principles of the invention indicate thatthe invention is effective with respect to all vertebrate species, including mammals, which are intended to be included in the term "patient". In this context, a mammal is understood to include any mammalian species in which treatment of diseases associated with angiogenesis is desirable, particularly agricultural and domestic mammalian species.

In another related embodiment, a tissue to be treated is a retinal tissue of a patient with diabetic retinopathy, macular degeneration or neovascular glaucoma and the angiogenesis to be inhibited is retinal tissue angiogenesis where there is neovascularization of retinal tissue.

In an additional related embodiment, a tissue to be treated is a tumor tissue of a patient with a solid tumor, a metastases, a skin cancer, a hemangioma or angiofibroma and the like cancer, and the angiogenesis to be inhibited is tumor tissue angiogenesis where there is neovascularization of a tumor tissue.

Inhibition of tumor tissue angiogenesis is a particularly preferred embodiment because of the important role neovascularization plays in tumor growth. In the absence of neovascularization of tumortissue, the tumor tissue does not obtain the required nutrients, slows in growth, ceases additional growth, regresses and ultimately becomes necrotic resulting in killing of the tumor. Stated differently, the present invention provides for a method of modulating tumor neovascularization by modulating tumor angiogenesis according to the present methods. Similarly, the invention provides a method of modulating tumor growth by practicing the angiogenesis-modulating methods.

The methods are also particularly effective against the formation of metastases because (1) their formation requires vascularization of a primary tumor so that the metastatic cancer cells can exit the primary tumor and (2) their establishment in a secondary site requires neovascularization to support growth of the metastases.

In a related embodiment, the invention contemplates the practice of the method in conjunction with othertherapies such as conventional chemotherapy directed against solid tumors and for control of establishment of metastases. The administration of angiogenesis inhibitor is typically conducted during or after chemotherapy, although it is preferably to inhibit angiogenesis after a regimen of chemotherapy at times where the tumor tissue will be responding to the toxic assault by inducing angiogenesis to recover by the provision of a blood supply and nutrients to the tumor tissue. In addition, it is preferred to administer the angiogenesis inhibition methods after surgery where solid tumors have been removed as a prophylaxis against metastases.

The present method for modulating angiogenesis in a tissue contemplates contacting a tissue in which angiogenesis is occurring, or is at risk for occurring, with a composition comprising a therapeutically effective amount of an ECRTP/DEP-1 receptor modulator capable of binding the ECRTP/DEP-1 receptor. Thus, the method comprises administering to a patient a therapeutically effective amount of a physiologically tolerable composition containing an ECRTP/DEP-1 receptor modulator of the invention.

The dosage ranges for the administration of the ECRTP/DEP-1 receptor modulator depend upon the form of the modulator, and its potency, as described further herein, and are amounts large enough to produce the desired effect in which angiogenesis and the disease symptoms mediated by angiogenesis are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can also be adjusted by the individual physician in the event of any complication.

A therapeutically effective amount is an amount of an ECRTP/DEP-1 receptor modulator sufficient to produce a measurable inhibition of angiogenesis in the tissue being treated, i.e., an angiogenesis-modulating amount. Inhibition of angiogenesis can be measured in situ by immunohistochemistry, as described herein, or by other methods known to one skilled in the art.

Insofar as an ECRTP/DEP-1 receptor modulator can take the form of an ECRTP/DEP-1 receptor ligand mimetic, and an anti-ECRTP/DEP-1 receptor monoclonal antibody, or fragment thereof, it is to be appreciated that the potency, and therefore an expression of a "therapeutically effective" amount can vary. However, as shown by the present assay methods, one skilled in the art can readily assess the potency of a candidate ECRTP/DEP-1 receptor modulator of this invention.

ECRTP/DEP-1 receptor modulator can be measured by a variety of means including inhibition of angiogenesis in the mouse corneal assay for angiogenesis described herein, binding of natural ligand or monoclonal antibody to an ECRTP/DEP-1 receptor as described herein, and the like assays.

A preferred ECRTP/DEP-1 receptor modulator has the ability to substantially bind to an ECRTP/DEP-1 receptor in solution at modulator concentrations of less than one (1) micro molar ($\mu$M), preferably less than 0.1 $\mu$M, and more preferably less than 0.01 $\mu$M. By "substantially" is meant that at least a 50 percent reduction in endothelial cell proliferation and migration is observed by modulation in the presence of the an ECRTP/DEP-1 receptor modulator, and at 50% reduction is referred to herein as an IC50 value.

A therapeutically effective amount of an ECRTP/DEP-1 receptor modulator of this invention in the form of a monoclonal antibody, or fragment thereof, is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml. For example, for Mab ECRTP/DEP-1 (MW=about 150 kDa), 10 $\mu$g/ml$\approx$67$\times 10^{-9}$ M. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

A therapeutically effective amount of an ECRTP/DEP-1 receptor modulator of this invention in the form of a polypeptide is typically an amount of polypeptide such that when administered in a physiologically tolerable composition is sufficient to achieve a plasma concentration of from about 0.001 microgram ($\mu$g) per milliliter (ml) to about 10 $\mu$g/ml, preferably from about 0.05 $\mu$g/ml to about 1.0 ug/ml. Based on a polypeptide having a mass of about 15,000 grams per mole (i.e. 15,000 Da), the preferred plasma concentration in molarity is from about 0.0001 micro molar ($\mu$M) to about 1 milli molar (mM). Stated differently, the dosage per body weight can vary from about 0.01 mg/kg to about 30 mg/kg, and preferably from about 0.05 mg/kg to about 20 mg/kg, in one or more dose administrations daily, for one or several days.

The monoclonal antibodies or polypeptides of the invention can be administered parenterally by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies or polypeptides of the invention can be administered intravenously, intraperitoneally, intramuscularly, subcutaneously, intra-cavity, transdermally, and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

C. Therapeutic Compositions

The present invention contemplates therapeutic compositions useful for practicing the therapeutic methods described herein. Therapeutic compositions of the present invention contain a physiologically tolerable carrier together with an ECRTP/DEP-1 receptor modulator as described herein, dissolved or dispersed therein as an active ingredient. In a preferred embodiment, the therapeutic ECRTP/DEP-1 receptor modulator composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an angiogenesis-modulating amount of an ECRTP/DEP-1 receptor modulator of the present invention, typically formulated to contain an amount of at least 0.1 weight percent of modulator per weight of total therapeutic composition. A weight percent is a ratio by weight of modulator to total composition. Thus, for example, 0.1 weight percent is 0.1 grams of inhibitor per 100 grams of total composition.

D. Modulators of ECRTP/DEP-1 Receptor

ECRTP/DEP-1 receptor modulators are used in the present methods for modulating ECRTP/DEP-1 receptor activity in tissues, including modulating angiogenesis in tissues. Thus, as used herein, the terms "modulate", "modulating", and "modulator" are meant to be construed to encompass inhibiting, blocking, promoting, stimulating, agonising, antagonizing, or otherwise affecting ECRTP/DEP-1 receptor activity in tissues.

Such modulators can take a variety of forms that include compounds which interact with the ECRTP/DEP-1 receptor in a manner such that functional interactions with natural ECRTP/DEP-1 ligands are mimicked, stimulated and/or inhibited. Exemplary modulators include analogs of an ECRTP/DEP-1 receptor natural ligand binding site on an ECRTP/DEP-1 receptor, mimetics of a natural ligand of an ECRTPIDEP-1 receptor that mimic the structural region involved in an ECRTP/DEP-1-receptor ligand binding interactions, polypeptides having a sequence corresponding to the domain of a natural ligand of an ECRTP/DEP-1 receptor, and antibodies which immunoreact with either an ECRTP/DEP-1 receptor or the natural ligand, all of which exhibit modulator activity as defined herein.

1. Polypeptides

In one embodiment, the invention contemplates ECRTP/DEP-1 receptor modulators in the form of polypeptides. A polypeptide (peptide) ECRTP/DEP-1 receptor modulator can have the sequence characteristics of either the natural ligand of the ECRTP/DEP-1 receptor or the ECRTP/DEP-1 receptor itself at the region involved in ECRTP/DEP-1 receptor-ligand interaction. A preferred ECRTP/DEP-1 receptor modulator peptide corresponds in sequence to the natural ligand.

Because antibody interactions with the ECRTP/DEP-1 receptor ectodomain modulate endothelial proliferation responses, the present invention contemplates the use of an isolated and purified ECRTP/DEP-1 receptor ectodomain, which is described in the Examples below, in the described methods as modulator for ECRTP/DEP-1 receptor activity. Such use reflects the contemplation that the ECRTP/DEP-1 receptor ectodomain is a homophilic, or "self" ligand, as discussed in the Examples below.

The term "ECRTP/DEP-1 receptor ectodomain" is contemplated to refer to ECRTP/DEP-1 receptor ectodomain fusion proteins and polypeptides, recombinant ECRTP/DEP-1 receptor ectodomain proteins and polypeptides, peptide derivatives, amides, conjugates with proteins, cyclized peptides, polymerized peptides, analogs, fragments, chemically modified peptides, and the like derivatives, as described below.

In one embodiment, a polypeptide of the present invention comprises no more than about 100 amino acid residues, preferably no more than about 60 residues, more preferably no more than about 30 residues. Peptides can be linear or cyclic.

It should be understood that a subject polypeptide need not be identical to the amino acid residue sequence of an ECRTP/DEP-1 receptor natural ligand or ECRTP/DEP-1 receptor ectodomain, so long as it includes required binding sequences and is able to function as an ECRTP/DEP-1 receptor moldulator in an assay such as is described herein.

A subject polypeptide includes any analog, fragment or chemical derivative of a polypeptide which is an ECRTP/DEP-1 receptor modulator. Such a polypeptide can be subject to various changes, substitutions, insertions, and deletions where such changes provide for certain advantages in its use. In this regard, an ECRTP/DEP-1 receptor modulator polypeptide of this invention corresponds to, rather than is identical to, the sequence of the natural ligand where one or more changes are made and it retains the ability to function as an ECRTP/DEP-1 receptor modulator in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of the natural ligand of the ECRTP/DEP-1 receptor in which one or more residues have been conservatively substituted with a functionally similar residue and which displays the ECRTP/DEP-1 receptor modulator activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of an ECRTP/DEP-1 receptor natural ligand, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues, but do not form ECRTP/DEP-1 receptor ligand epitopes. Typical amino acid residues used for linking are tyrosine, cysteine, lysine, glutamic and aspartic acid, or the like. In addition, a subject polypeptide can differ, unless otherwise specified, from the natural sequence of an ECRTP/DEP-1 receptor ligand by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W.H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv Enzymol*, 32:221–96, 1969; Fields et al., *Int. J. Peptide Protein Res.*, 35:161–214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for cyclizing peptides is described by Zimmer et al., *Peptides* 1992, pp. 393–394, ESCOM Science Publishers, B.V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

2. Monoclonal Antibodies

The present invention describes, in one embodiment, ECRTP/DEP-1 receptor modulators in the form of monoclonal antibodies which immunoreact with an ECRTP/DEP-1 receptor and bind the ECRTP/DEP-1 receptor to modulate receptor activity as described herein. The invention also describes cell lines which produce the antibodies, methods for producing the cell lines, and methods for producing the monoclonal antibodies.

A monoclonal antibody of this invention comprises antibody molecules that 1) immunoreact with isolated ECRTP/DEP-1 receptor, and 2) bind to the ECRTP/DEP-1 receptor to modulate its biological function. Preferred monoclonal antibodies which preferentially bind to ECRTP/DEP-1 receptor include a monoclonal antibody having the immunoreaction characteristics of Mab ECRTPAb-1, having molecular weight of about 150 KDa respectively and which binds to the ectodomain of the ECRTP/DEP-1 receptor, as is described herein below. Mab ECRTPAb-1 is preferably secreted by hybridoma cell line ATCC HB12570. The hybridoma cell line ATCC HB12570 was deposited pursuant to Budapest Treaty requirements with the American Type Culture Collection (ATCC), Manassas, Va., U.S.A. on Sep. 18, 1998.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments.

Indeed, as described in the Examples set forth below, an Fab fragment, that is, a monovalent fragment, of the Mab ECRTPAb-1 releases density arrest. Thus, it is contemplated to be within the scope of the present invention that such a monovalent modulator is used to promote angiogenesis, or to promote endothelial cell migration and proliferation, or to release inhibitory influences on endothelial cells to serve as an adjunctive to other angiogenic stimuli. Thus, the terms "modulate", "modulating", and "modulator" are meant to be construed to encompass such promotion.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495–497 (1975), which description is incorporated by reference. Additional methods are described by Zola, *Monoclonal Antibodies: a Manual of Techniques*, CRC Press, Inc. (1987). The hybridoma supernates so prepared can be screened for the presence of antibody molecules that immunoreact with an ECRTP/DEP-1 receptor and for inhibition of an ECRTP/DEP-1 receptor to activate its biological function.

Briefly, to form the hybridoma from which the monoclonal antibody composition is produced, a myeloma or other self-perpetuating cell line is fused with lymphocytes obtained from the spleen of a mammal hyperimmunized with a source of an ECRTP/DEP-1 receptor, such as an ECRTP/DEP-1 receptor isolated from M21 human melanoma cells as described by Cheresh et al., *J. Biol Chem*, 262:17703–17711 (1987).

It is preferred that the myeloma cell line used to prepare a hybridoma be from the same species as the lymphocytes. Typically, a mouse of the strain 129 GlX+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the ATCC, Manassas, Va., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by well known techniques. Media useful for the preparation of these compositions are both well known in the art and commercially available and include synthetic culture media, inbred mice and the like. An exemplary synthetic medium is Dulbecco's minimal essential medium (DMEM—Dulbecco et al., *Virol* 8:396 (1959)) supplemented with 4.5 gm/l glucose, 20 mM glutamine, and 20% fetal calf serum. An exemplary inbred mouse strain is the Balb/C.

Other methods of producing a monoclonal antibody, a hybridoma cell, or a hybridoma cell culture are also well known. See, for example, the method of isolating monoclonal antibodies from an immunological repertoire as described by Sastry, et al., *Proc Natl Acad Sci USA* 86:5728–5732 (1989); and Huse et al., *Science* 246:1275–1281 (1989).

Also contemplated by this invention is the hybridoma cell, and cultures containing a hybridoma cell that produce a monoclonal antibody of this invention. Particularly preferred is the hybridoma cell line that secretes monoclonal antibody Mab ECRTPAb-1 as described in the Examples presented below and as designated ATCC HB12570. Mab ECRTPAb-1 was prepared as described in the Examples. The invention thus contemplates, in one embodiment, a monoclonal antibody that has the immunoreaction characteristics of Mab ECRTPAb-1.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a preselected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention contemplates, in one embodiment, a monoclonal antibody of this invention that is humanized by grafting to introduce components of the human immune system without substantially interfering with the ability of the antibody to bind antigen.

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein, such as ECRTP/DEP-1.

3. Other Modulators

It is also contemplated that previously described angiogenesis inhibiting chemical compounds are modulators of ECRTP/DEP-1 receptor activity in tissues. Examples of such compounds include, but are not limited to, angiostatin, endostatin and thrombospondin. Accordingly, such compounds may be used in the modulation of ECRTP/DEP-1 receptor activity in tissues, according to the methods of the present invention.

Given the disclosure of the ECRTP/DEP-1 receptor activity in tissues herein, it is also contemplated that as yet undefined chemical compounds may be used to modulate ECRTP/DEP-1 receptor activity in tissues in accordance with the methods of the present invention. The identification of such compounds is facilitated by the description of screening assays directed to ECRTP/DEP-1 receptor activity in tissues presented below.

D. Screening Assay

Skilled artisans will understand that the disclosure herein of the localization and function of the ECRTP/DEP-1 receptor, and in vitro assays relating to such localization and function, provides opportunities to screen for compounds that modulate, whether partially or completely, the functional activity of the ECRTP/DEP-1 receptor. In this context, "modulate" is intended to mean that the subject compound increases or decreases one or more functional activities of the ECRTP/DEP-1 receptor.

Further, the screening assays illustrated in the Examples below include biochemical assays (e.g., measuring effects of anti-ECRTP/DEP-1 receptor monoclonal antibodies on ECRTP/DEP-1 receptor activity), and cellular in vitro assays (e.g., measuring the effects of ECRTP/DEP-1 receptor overexpression on endothelial cell proliferation and migration). The illustrative biochemical assays may be particularly useful in screening for compounds modulating an ECRTP/DEP-1 receptor activity, while the cellular assays may be particularly useful in screening for compounds completely altering an ECRTP/DEP-1 receptor activity. Thus, until the disclosure herein of the role of the ECRTP/DEP-1 receptor in regulating endothelial cell proliferation and migration and in regulating angiogenesis, a motivation to screen for compounds that modulate ECRTP/DEP-1 receptor activity was lacking in the prior art.

Those skilled in the art will understand that binding of a ligand at a molecular binding site can be modulated in a direct matter (e.g., by blocking the site), as well as modulated in an indirect manner (e.g., by conformational changes induced following binding of a second, i.e., different, ligand at a distant site). In this regard, it is likely that the binding site specificity of an ECRTP/DEP-1 receptor for its endogenous ligand can be completely modulated or altered (i.e., to bind a different ligand) by agents that bind at distant sites in the ECRTP/DEP-1 receptor. Examples of compounds that may be screened in the latter several assays include at least nucleic acids (e.g., DNA oligonucleotide aptamers that bind proteins and alter their functions), proteins, carbohydrates, lectins, organic chemicals, and the like. Such screening assays may be useful for identifying candidate therapeutic agents that may provide drugs useful in animals and humans.

It is still further understood that due to the significance of the ECRTP/DEP-1 receptor in endothelial cell migration and proliferation, in density induced growth arrest, and in modulation of angiogenesis, innate regulatory mechanisms exist in cells for regulating their activity by binding to an ECRTP/DEP-1 receptor, or to complexes containing an ECRTP/DEP-1 receptor. Such regulatory factors can include, at least: (a) cofactors that bind to the complex and exert regulatory action by destabilizing or stabilizing the complex; (b) agents that modulate or alter the activity of the complex by inducing confirmational changes in the ECRTP/DEP-1 receptor as they are bound in a complex; (c) enzymes that inactivate one or both members of a complex; and (d) cellular control factors (e.g., signal transduction second messengers, transcription regulating factors, DNA replication factors and the like) that bind an ECRTP/DEP-1 receptor or ECRTP/DEP-1 receptor complexes and modulate or alter functional activity. Those skilled in the art will recognize that the functional regions of an ECRTP/DEP-1 receptor represent particularly attractive targets for three-dimensional molecular modeling and for construction of mimetic compounds, e.g., organic chemicals constructed to mimic the three-dimensional interactions between the ECRTP/DEP-1 receptor and its endogenous binding partner, or other binding partner.

Thus, the present invention contemplates a process of screening substances for their ability to modulate or alter endothelial cell migration and proliferation, density induced growth arrest and/or angiogenesis comprising the steps of providing a cell that contains a functional ECRTP/DEP-1 receptor and testing the ability of selected substances to modulate or alter migration or proliferation of that cell, density induced growth arrest of the cell, or initiation of angiogenesis in the cell.

Utilizing the methods and compositions of the present invention, screening assays for the testing of candidate substances can be derived. A candidate substance is a substance which potentially can modulate endothelial cell migration and proliferation, density induced growth arrest and/or angiogenesis, by binding or other intramolecular interaction, with an ECRTP/DEP-1 receptor that modulates endothelial cell migration and proliferation, density induced growth arrest and angiogenesis.

A screening assay of the present invention generally involves determining the ability of a candidate substance to affect endothelial cell migration and proliferation, density induced growth arrest and/or angiogenesis in a target cell, such as the screening of candidate substances to identify those that modulate or alter endothelial cell migration and proliferation, density induced growth arrest and/or angiogenesis. Target cells can be either naturally occurring cells known to contain an ECRTP/DEP-1 receptorortransformed cell produced in accordance with a process of transformation set forth herein and as are known in the art.

As is well known in the art, a screening assay provides a cell under conditions suitable for testing modulation or alteration of endothelial cell migration and proliferation, density induced growth arrest and/or angiogenesis. These conditions include but are not limited to pH, temperature, tonicity, the presence of relevant factors involved in the cell cycle (e.g., growth factors), and relevant modifications to the polypeptide such as glycosylation or prenylation. It is contemplated that an ECRTP/DEP-1 receptor can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of endothelial cell migration and proliferation, density induced growth arrest and/or angiogenesis in specific cells. Such factors include, for example, the presence and absence (withdrawal) of growth factor, interleukins, or colony stimulating factors.

E. Methods For Identifying Modulators of an ECRTP/DEP-1 Receptor

The invention thus also pertains to assay methods for identifying candidate an ECRTP/DEP-1 receptor modulators. In these assay methods candidate molecules are evaluated for their potency in agonising an ECRTP/DEP-1 receptor binding to natural ligands, and furthermore are evaluated for their potency in modulating angiogenesis in a tissue.

An exemplary assay measures angiogenesis in the chick chorioallantoic membrane (CAM) and is referred to as the CAM assay. The CAM assay has be described in detail by others, and further has been used to measure both angiogenesis and neovascularization of tumor tissues. See Ausprunk et al., *Am J Pathol* 79:597–618 (1975) and Ossonski et al., *Cancer Res* 40:2300–2309 (1980).

The CAM assay is a well recognized assay model for in vivo angiogenesis because neovascularization of whole tissue is occurring, and actual chick embryo blood vessels are growing into the CAM or into the tissue grown on the CAM. The CAM assay illustrates inhibition of neovascularization based on both the amount and extent of new vessel growth. Furthermore, it is easy to monitor the growth of any tissue transplanted upon the CAM, such as a tumor tissue. Finally, the assay is particularly useful because there is an internal control for toxicity in the assay system. The chick embryo is exposed to any test reagent, and therefore the health of the embryo is an indication of toxicity.

F. Preparation of Targeting Agent/toxin Compounds, Including Immunotoxins

Methods for the production of the target agent/toxin agent compounds of the invention are described herein. The targeting agents, such as antibodies, of the invention may be linked, or operatively attached, to the toxins of the invention by either crosslinking orvia recombinant DNA techniques, to produce, for example, targeted immunotoxins.

While the preparation of immunotoxins is, in general, well known in the art (see e.g., U.S. Pat. Nos. 4,340,535 and 5,776,427, and EP 44167, each of which incorporated herein by reference), certain advantages may be achieved through the application of certain preferred technology, both in the preparation of the immunotoxins and in their purification for subsequent clinical administration. For example, while numerous types of disulfide-bond containing linkers are known which can successfully be employed to conjugate the toxin moiety with the targeting agent, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

A wide variety of cytotoxic agents are known that may be conjugated to anti-endothelial cell antibodies. Examples include numerous useful plant-, fungus- or even bacteria-derived toxins, which, by way of example, include various A chain toxins, particularly ricin A chain, ribosome inactivating proteins such as saporin or gelonin, a -sarcin, aspergillin, restrictocin, ribonucleases such as placental ribonuclease, angiogenic, diphtheria toxin, and pseudomonas exotoxin, to name just a few.

However, it may be desirable from a pharmacologic standpoint to employ the smallest molecule possible that nevertheless provides an appropriate biological response. One may thus desire to employ smaller-chain peptides which will provide an adequate anti-cellular response.

Alternatively, one may find that the application of recombinant DNA technology to the toxin moiety will provide additional significant benefits in accordance the invention. For example, the cloning and expression of biologically active toxin candidates has now been described through the publications of others (O'Hare et al., *FEBS Lett* 210:731 (1987); Lamb et al., *Eur Jrnl Biochem* 148:265–270 (1985); Hailing et al., *Nucl Acids Res* 13:8019–8033 (1985)), it is now possible to identify and prepare smaller or otherwise variant peptides which nevertheless exhibit an appropriate toxin activity. Moreover, the use of cloned toxin candidates allows the application of site-directed mutagenesis, through which one can readily prepare and screen for mutated peptides and obtain additional useful moieties for use in connection with the present invention.

In cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including the particular cross-linking reagent used and the structures that are cross-linked, will be of some significance.

Cross-linking reagents are used to form molecular bridges that tie together functional groups of two different proteins (e.g., a toxin and a binding agent). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein.

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

An exemplary cross-linking reagent is SMPT, which is a bifunctional cross-linker containing a disulfide bond that is "sterically hindered" by an adjacent benzene ring and methyl groups. It is believed that stearic hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido)ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane (Thorpe et al., *Cancer Res* 47:5924–5931 (1987)). The use of such cross-linkers is well understood in the art.

Once conjugated, it will be important to purify the conjugate so as to remove contaminants such as unconjugated toxin or targeting agent. It is important to remove unconjugated targeting agent to reduce undesired toxicity and to avoid the possibility of competition for the antigen between conjugated and unconjugated species. In general, the most preferred purification technique will incorporate the use of Blue-Sepharose with a gel filtration or gel permeation step. Blue-Sepharose is a column matrix composed of Cibacron Blue 3GA and agarose, which has been found to be useful in the purification of immunoconjugates (Knowles & Thorpe, *Anal. Biochem* 120:440–443 (1987)). The use of Blue-Sepharose combines the properties of ion exchange with toxin binding to provide good separation of conjugated toxin from non-conjugated toxin. The Blue-Sepharose column allows the elimination of the free (non-conjugated) targeting agent (e.g., the antibody or fragment) from the conjugate preparation. To eliminate the free (non-conjugated) toxin a molecular exclusion chromatography step is preferred using either conventional gel filtration procedure or high performance liquid chromatography.

Standard recombinant DNA techniques that are well known to those of skill in the art may be utilized to express nucleic acids encoding the targeting agent/toxin compounds of the invention. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., Molecular Cloning, A Laboratory Manual, Cold Spring Harbor Laboratory, N.Y. (1989); and Ausubel et al., Current Protocols in Molecular Biology, Greene Publishing Associates and Wiley Interscience, N.Y. (1989).

When produced via recombinant DNA techniques such as those described herein, the targeting agent/toxin compounds of the invention may be referred to herein as "fusion proteins". It is to be understood that such fusion proteins contain at least a targeting agent and a toxic moiety operatively attached, such that the fusion protein may be used in accordance with the methods of the present invention. The fusion proteins may also include additional peptide sequences, such as peptide spacers which operatively attach the targeting agent and toxin compound, as long as such additional sequences do not appreciably affect the targeting or toxin activities of the fusion protein.

Depending on the specific toxin compound used as part of the fusion protein, it may be necessary to provide a peptide spacer operatively attaching the targeting agent and the toxin compound which is capable of folding into a disulfide-bonded loop structure. Proteolytic cleavage within the loop would then yield a heterodimeric polypeptide wherein the targeting agent and the toxin compound are linked by only a single disulfide bond. See e.g., Lord et al., *In Genetically Engineered Toxins* (Ed. A. Frank, M. Dekker Publ., p. 183) (1992). An example of such a toxin is a Ricin A-chain toxin.

When certain other toxin compounds are utilized, a non-cleavable peptide spacer may be provided to operatively attach the targeting agent and the toxin compound of the fusion protein. Toxins which may be used in conjunction with non-cleavable peptide spacers are those which may, themselves, be converted by proteolytic cleavage, into a cytotoxic disulfide-bonded form (see e.g., Ogata et al., *J Biol Chem* 256:20678–20685 (1990)). An example of such a toxin compound is a Pseudomonas exotoxin compound.

Nucleic acids that may be utilized herein comprise nucleic acid sequences that encode a targeting agent of interest and nucleic acid sequences that encode a toxin agent of interest. Such target agent-encoding and toxin agent-encoding nucleic acid sequences are attached in a manner such that translation of the nucleic acid yields the targeting agent/toxin compounds of the invention.

Standard techniques, such as those described above may be used to construct expression vectors containing the above-described nucleic acids and appropriate transcriptional/translational control sequences. A variety of host-expression vector systems may be utilized. These include but are not limited to microorganisms such as bacteria (e.g., E. coli, B. subtilis) transformed with recombinant bacteriophage DNA, plasmid DNA or cosmid DNA expression vectors containing targeting agent/toxin coding sequences; yeast (e.g., Saccharomyces, Pichia) transformed with recombinant yeast expression vectors containing targeting agent/toxin coding sequences; insect cell systems infected with recombinant virus expression vectors (e.g., baculovirus) containing the targeting agent/toxin coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the targeting agent/toxin coding sequences coding sequence; or mammalian cell systems (e.g., COS, CHO, BHK, 293, 3T3) harboring recombinant expression constructs containing promoters derived from the genome of mammalian cells (e.g., metallothionein promoter) orfrom mammalian viruses (e.g., the adenovirus late promoter; the vaccinia virus 7.5 K promoter; lentiviral vectors).

In bacterial systems a number of expression vectors may be advantageously selected depending upon the use intended for the targeting agent/toxin compound being expressed. For example, when large quantities of targeting agent/toxin compound are to be produced for the generation of antibodies or to screen peptide libraries, vectors which direct the expression of high levels of fusion protein products that are readily purified may be desirable. Such vectors include but are not limited to the E. coli expression vector pUR278 (Ruther et al., EMBO J 2:1791 (1983)), in which the targeting agent/toxin coding sequence may be ligated individually into the vector in frame with the lac Z coding region so that a fusion protein additionally containing a portion of the lac Z product is provided; pIN vectors (Inouye et al., Nucleic Acids Res 13:3101–3109 (1985); Van Heeke et al., J Biol Chem 264:5503–5509 (1989)); and the like. pGEX vectors may also be used to express foreign polypeptides, such as the targeting agent/toxin compounds as fusion proteins additionally containing glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the targeting agent/toxin protein of the fusion protein can be released from the GST moiety.

In an insect system, Autograph californica nuclear polyhidrosis virus (AcNPV) is used as a vector to express foreign genes. The virus grows in Spodoptera frugiperda cells. The targeting agent/toxin coding sequences may be cloned into non-essential regions (for example the polyhedrin gene) of the virus and placed under control of an AcNPV promoter (for example the polyhedrin promoter). Successful insertion of the targeting agent/toxin coding sequences will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (see e.g., Smith et al., J Virol 46:584 (1983); U.S. Pat. No. 4,215,051).

In mammalian host cells, a number of viral based expression systems may be utilized. In cases where an adenovirus is used as an expression vector, the targeting agent/toxin coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing targeting agent/toxin proteins in infected hosts (see e.g., Logan et al., *Proc Natl Acad Sci USA* 81:3655–3659 (1984)). Specific initiation signals may also be required for efficient translation of inserted targeting agent/toxin coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol* 153:516–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, etc. For long-term, high-yield production of recombinant proteins, stable expression is preferred. For example, cell lines which stably express constructs encoding the targeting agent/toxin compounds may be engineered. Rather than using expression vectors which contain viral origins of replication, host cells can be transformed with targeting agent/toxin DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for one or two (1–2) days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., *Cell* 11:223 (1977)), hypoxanthine-guanine phosphoriboxyltransferase (Szybalska et al., *Proc Natl Acad Sci USA* 48:2026 (1962)), and adenine phosphoribosyltransferase genes (Lowy et al., *Cell* 22:817 (1980)) can be employed in tk-, hgprt- or aprt-cells, respectively. Also, antimetabolite resistance can be used as the basis of selection for dhfr, which confers resistance to methotrexate (Wigler et al., *Proc Natl Acad Sci USA* 77:3567 (1980); O'Hare et al., *Proc Natl Acad Sci USA* 78:1527 (1981)); gpt, which confers resistance to mycophenolic acid (Mulligan et al., *Proc Natl Acad Sci USA* 78:2072 (1981)); neo, which confers resistance to the aminoglycoside G-418 (Colberre-Garapin et al., *J Mol Biol* 150:1 (1981)); and hygro, which confers resistance to hygromycin (Santerre et al., *Gene* 30:147 (1984)).

After a sufficiently purified compound has been prepared, one will desire to prepare it into a pharmaceutical composition that may be administered parenterally. This is done by using for the last purification step a medium with a suitable pharmaceutical composition.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate. Such formulations will typically include buffers such as phosphate buffered saline (PBS), or additional additives such as pharmaceutical excipients, stabilizing agents such as BSA or HSA, or salts such as sodium chloride. For parenteral administration it is generally desirable to further render such compositions pharmaceutically acceptable by insuring their sterility, non-immunogenicity and non-pyrogenicity. Such techniques are generally well known in the art as exemplified by *Remington's Pharmaceutical Sciences*, 16th Ed. Mack Publishing Company (1980), incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

A preferred parenteral formulation of the targeting agent/toxin compounds, including immunotoxins, in accordance with the present invention is 0.25 to 2.5 mg conjugate/ml in 0.15 M NaCl aqueous solution at pH 7.5 to 9.0. The preparations may be stored frozen at −10° C. to −70° C. for at least one (1) year.

G. Attachment of Other Agents to Targeting Agents

It is contemplated that most therapeutic applications of the present invention will involve the targeting of a toxin moiety to the endothelium, particularly tumor endothelium. This is due to the much greater ability of most toxins to deliver a cell killing effect as compared to other potential agents. However, there may be circumstances, such as when the target antigen does not internalize by a route consistent with efficient intoxication by targeting agent/toxin compounds, such as immunotoxins, where one will desire to target chemotherapeutic agents such as antitumor drugs, other cytokines, antimetabolites, alkylating agents, hormones, and the like. The advantages of these agents over their non-targeting agent conjugated counterparts is the added selectivity afforded by the targeting agent, such as an antibody. Exemplary agents include, but are not limited to, such as steroids, cytosine arabinoside, methotrexate, aminopterin, anthracyclines, mitomycin C, vinca alkaloids, demecolcine, etoposide, mithramycin, and the like. This list is, of course, merely exemplary in that the technology for attaching pharmaceutical agents to targeting agents, such as antibodies, for specific delivery to tissues is well established.

It is proposed that particular benefits may be achieved through the application of the invention to tumor imaging. Imaging of the tumor vasculature is believed to provide a major advantage when compared to present imaging techniques, in that the cells are readily accessible. Moreover, the technology for attaching paramagnetic, radioactive and even fluorogenic ions to targeting agents, such as antibodies, is well established. Many of these methods involve the use of a metal chelate complex employing, for example, an organic chelating agent such a DTPA attached to the antibody. See e.g., U.S. Pat. No. 4,472,509. In the context of the present invention the selected ion is thus targeted to the tumor endothelium by the targeting agent, such as an antibody, allowing imaging to proceed by means of the attached ion.

A variety of chemotherapeutic and other pharmacologic agents have now been successfully conjugated to antibodies and shown to function pharmacologically (see e.g., Vaickus et al., *Cancer Invest* 9:195–209 (1991)). Exemplary antineoplastic agents that have been investigated include doxorubicin, daunomycin, methotrexate, vinblastine, and various others. Diliman et al., *Antibody Immunocon Radiopharm* 1:65–77 (1988); Pietersz et al., *Antibody Immunoconj Radiopharm* 1:79–103 (1988). Moreover, the attachment of other agents such as neocarzinostatin (Kimura et al., *Immunogenetics* 11:373–381 (1980)), macromycin, trenimon (Ghose et al., *Meth. Enzymology* 93:280–333 (1983)) and α-amanitin has been described.

In addition to chemotherapeutic agents, the invention is contemplated to be applicable to the specific delivery of a wide variety of other agents to tumor vasculature. For example, under certain circumstances, one may desire to deliver a coagulant such as Russell's Viper Venom, activated Factor IX, activated Factor X or thrombin to the tumor vasculature. This will result in coagulation of the tumor's blood supply. One can also envisage targeting a cell surface lytic agent such as phospholipase C, (Flickinger & Trost, *Eu. J. Cancer* 12(2):159–60 (1976)) or cobra venom factor (CVF) (Vogel & Muller-Eberhard, *Anal. Biochem* 118(2) :262–268 (1981)) which should lyse the tumor-endothelial cells directly. The operative attachment of such structures to targeting agents, such as antibodies, may be readily accomplished, for example, by protein-protein coupling agents such as SMPT. Moreover, one may desire to target growth factors, other cytokines or even bacterial endotoxin or the lipid A moiety of bacterial endotoxin to a selected cell type, in order, e.g., to achieve modulation of cytokine release. The attachment of such substances is again well within the skill in the art as exemplified by Ghose et al., *CRC Critical Reviews in Therapeutic Drug Carrier Systems* 3:262–359 (1987).

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent as described above. In the case of doxorubicin and daunomycin, attachment may be achieved by means of an acid labile acyl hydrazone or cis aconityl linkage between the drug and the antibody. Finally, in the case of methotrexate or aminopterin, attachment is achieved through a peptide spacer such as L-Leu-L-Ala-L-Leu-L-Ala, between the γ-carboxyl group of the drug and an amino acid of the antibody.

Alternatively, any such structures which are nucleic acid-encoded structures may be operatively attached to the targeting agents of the invention by standard recombinant DNA techniques, such as, for example, those discussed above.

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

EXAMPLE 1

Endothelial Localization of Receptor Tyrosine Phosphatase, ECRTP/DEP-1, In Developing and Mature Renal Vasculature Developmental assembly of the renal microvasculature is a precise process requiring spatially and temporally coordinated migration, assembly, differentiation and maturation of endothelial cells in the context of adjacent epithelial and mesangial cells. Molecular determinants of assembly are largely undefined, yet requirements for cell surface receptors to direct context appropriate endothelial responses are anticipated. Endothelial expression and distribution of the receptor tyrosine phosphatase, ECRTP/DEP-1, were evaluated during developmental assembly of the renal microvasculature. Monoclonal antibodies generated against ECRTP/DEP-1 ectodomain epitopes localize its expression to membrane surfaces of endothelial cells in glomerular, peritubular capillary and arterial renal circulations of mature human and murine kidney. During kidney development, ECRTP/DEP-1 receptor immunostaining is evident on a subpopulation of metanephric mesenchymal cells and on putative progenitors of glomerular capillary endothelial cells early in their recruitment to developing glomeruli. ECRTP/DEP-1 receptor is prominently displayed on luminal membrane surfaces with punctate accumulations at inter-endothelial contacts that overlap, but do not co-localize with VE cadherin. In vitro studies show that ECRTP/DEP-1 receptor is recruited to positions of inter-endothelial contact in confluent cultured human renal and dermal microvascular endothelial cells, where its distribution overlaps, but again does not coincide with VE cadherin. Experimental dissociation of VE cadherin from endothelial junctional complexes does not redistribute ECRTP/DEP-1 away from inter-endothelial contacts. These findings indicate that ECRTP/DEP-1 ectodomains interact with proteins that are expressed on surfaces of endothelial cells and that are engaged by cell-cell contact, to convey signals for cell recognition, or arrest of migration or proliferation.

In order to identify receptor tyrosine phosphatases expressed in human renal microvascular endothelial cells (HRMEC), degenerate oligonucleotide primers derived from conserved phosphatase domains were used to amplify and sequence cDNAs representing expressed messages, according to methods described in Schoecklmann et al., *J Am Soc Nephrol* 5:730 (1994)(abstract). Among putative receptor cDNAs identified was one we designated ECRTP (endothelial cell receptor tyrosine phosphatase), a product virtually identical to the DEP-1 (for density enhanced phosphatase) cDNA cloned by Ostman et al. from HeLa cells and regulated in abundance by cell density in WI-38 cells. Ostman et al., *Proc Natl Acad Sci USA* 91:9680–9684 (1994). ECRTP/DEP-1 receptor (also called byp-1, HPTPh, and CD148) expression has been identified in neonatal smooth muscle cells, in breast and thryoid cancer cell lines, and in all hematopoietic lineages. Keane et al., *Cancer Research* 56:4236–4243 (1996); de la Fuente-Garcia et al., *Blood* 91:2800–2809 (1998). Although ECRTP/DEP-1 expression was identified in arterial endothelial cells of the kidney, in situ hybridization experiments failed to detect glomerular capillary localization of ECRTP/DEP-1 mRNA. Borges et al., *Circulation Research* 79:570–580 (1996). The developmental timing and distribution of its expression have not been previously reported.

Like other members of the Class III receptor tyrosine phosphatase family, including GLEPP-1, SAP-1, and DPTP 10D, ECRTP/DEP-1 receptor is a type I membrane protein characterized by a large extracellular domain containing eight or more fibronectin type III repeats and a single cytoplasmic domain phosphatase catalytic domain. Ostman et al., *Proc Natl Acad Sci USA* 91:9680–9684 (1994). The GLEPP-1 receptor tyrosine phosphatase is structurally similar to ECRTP/DEP-1, yet shows renal expression limited to glomerular visceral epithelial cells, where it has been implicated in podocyte integrity. Thomas et al., *J Biol Chem* 269:19953–19962 (1994). Unlike the MAM domain containing receptors, PTP m and k, available data do not support participation of class III receptors in homophilic binding, and ligands have not yet been identified.

Monoclonal antibodies were developed against ECRTP/DEP-1 receptor ectodomain epitopes to characterize its distribution in the renal circulation of mature and developing kidney. ECRTP/DEP-1 receptor is expressed at high levels in glomerular, peritubular and renal arterial endothelial cells and shows a pattern of distribution in vivo and in vitro that suggests it contributes to cell-cell recognition required for capillary assembly and maintenance.

METHODS

Cell Lines and Cell Culture

Primary human renal microvascular endothelial cells (HRMEC) were isolated, cultured, and used at third or fourth passage after thawing, as described. Martin et al., In Vitro *Cell Dev Biol* 33:261–269 (1997). Human dermal microvascular endothelial cells (HMEC-1 cells, CDC) were grown in MCDB131 media (Sigma) containing 15% fetal bovine serum (Hyclone Laboratories, Logan Utah, USA), 10 ng/ml epidermal growth factor (Collaborative Biomedical Products; Becton Dickinson, Bedford, Mass.), and 1 mg/ml hydrocortisone (Sigma) Ades et al., *J Invest Dermatol.* 99:683–690 (1992). Madin Darby Canine Kidney (MDCK) cells (kindly provided by L. Limbird, Vanderbilt Pharmacology) were grown in Dulbecco's minimal essential medium (DMEM, GIBCO BRL) containing 4.5% D-glucose and supplemented with 10% fetal bovine serum. All growth medium was supplemented with 1 mM L-glutamine (GIBCO BRL), 100 units/ml penicillin and 100 mg/ml streptomycin (GIBCO BRL).

Generation of Antibodies to Recombinant ECRTP/DEP-1 Proteins

Ectodomain (amino acids 175–536) and catalytic domain (amino acids 1048–1338) sequences of human, ECRTP/DEP-1 receptor. Ostman et al., *Proc Natl Acad Sci USA* 91:9680–9684 (1994), were subcloned into the pRSET vector (Invitrogen, Carlsland, Calif.). Recombinant fusion proteins were expressed in bacteria, purified by NI-AGAROSE AFFINITY (Invitrogen), and characterized by SDS-PAGE as greater than 95% homogeneous proteins of 40 and 36 kDa, respectively. Mouse hybridoma antibodies (ECRTP-Ab1, ECRTP-Ab2) were generated against ECRTP/DEP-1 receptor ectodomain (ECRTP/DEP-1$_{ec}$) protein by intraperitoneal immunization, fusion with SP2-0 cells, ELISA screening, selection, expansion and purification by affinity chromatography on PROTEIN A-AGAROSE (Sigma).
Immunodetection of Exogeneously Expressed ECRTP/DEP-1 Receptor MDCK cells grown in 100 mm plastic dishes (Falcon) were transfected with an expression plasmid pSRa DEP-⅓× HA that drives high level expression of the human ECRTP/DEP-1 receptor modified by addition of three repeats of a hemagglutinin peptide (HA) to the carboxy terminus, using cationic lipid (LIPOFECTAMINE™, GIBCO BRL) according to the manufacturer's protocol. Forty eight hours aftertransfection, cells were placed on ice, washed twice with ice cold PBS(−) and immediately lysed in 0.5 ml lysis buffer (50 mM HEPES pH 7.5, 50 mM NaCl, 5 mM EDTA, 2 μg/ml aprotinin, 1 μg/ml leupeptin, 1 mM PMSF). Lysates were clarified by centrifugation, and membrane receptors were recovered by batch adsorption to WGA-Agarose (Sigma) for 4 hours at 4° C. The resultant precipitates were resolved by 7% SDS-PAGE under reducing conditions, transferred to Immobilon-P transfer membranes (Millipore), and blocked in 5% non-fat dry milk in Tris-buffered saline (50 mM Tris HCl pH 7.5, 137 mM NaCl) containing 0.2% Tween 20 (TBST) overnight at 4° C. Blots were incubated with murine monoclonal ECRTPAbs 1 or 2 (10 μg/ml) or anti-HA (2.5 μg/ml) antibody followed by incubation with horseradish peroxidase-conjugated rabbit anti-mouse IgG antibody (Boehringer Mannheim). Membranes were washed with TBST, then developed using a chemiluminescent substrate (ECL, Amersham Corp.) according to the manufacturer's instructions.
Generation of Stably Transfected MDCK Cells and Cell Staining MDCK cells were transfected with an expression plasmid pCDNA3 DEP⅓×HA (Invitrogen) using cationic lipids (Lipofectamine™, GIBCO BRL) according to the manufacturers protocol. Stable transfectants were selected by addition of G418 (GIBCO BRL) to culture media at a final concentration of 800 μg/ml, and a single colony was obtained by limited dilution cloning. The cells were grown on glass coverslips (Fisher) and fixed with 100% methanol for 10 min at −20° C. Coverslips were washed with phosphate buffered saline, blocked with 5% goat serum for 30 min at room temperature, incubated with ECRTPAb-2 (10 μg/ml) for 60 min, washed, then incubated with FITC conjugated goat anti-mouse IgG (Jackson Immunoresearch Laboratory Inc.) for 60 min. Coverslips were mounted and analyzed by confocal microscopy (Zeiss LSM410). To preabsorb the immunoreactivity of ECRTP/DEP-1-Ab, 50 μg of ECRTP/DEP-1 proteins (Ec or Cy) were preincubated with ECRTPAb-2 for 4 hours at 4° C., microcentrifuged at 15,000 rpm for 20 min and the resultant supernatant was used to stain cells.
Tissue Immunolocalization Human kidney tissue was snap-frozen in a dry ice-acetone bath. Cryostat sections (4 mm) were fixed in acetone at −20° C. for 10 min, washed with phosphate buffered saline, and pre-adsorbed with avidin-biotin blocking reagents (Vector Laboratories) according to manufacturer's instructions. Sections were washed with phosphate buffered saline, blocked with 5% goat serum, incubated with monoclonal ECRTP/DEP-1 receptor antibody (ECRTP-Ab1, 10 μg/ml, 10 min), washed, incubated with biotinylated goat anti-mouse IgG (Vector Laboratories, 7.5 μg/ml, 60 min), washed, incubated with fluorescein isothiocyanate (FITC)-conjugated streptavidin (Pierce, 4 μg/ml, 30 min) and finally washed with phosphate buffered saline. Coverslips were mounted (Vectashield, Vector) and analyzed by confocal microscopy (Zeiss LSM410). For co localization experiments, acetone fixed frozen sections were blocked with 5% donkey serum, and incubated with mixture of ECRTP/DEP-1 receptor antibody (10 μg/ml) and goat VE cadherin antibody (5 μg/ml, Santa Cruz Biotechnology Inc.) at room temperature for 60 minutes. Specific antibodies were detected using a mixture of FITC-conjugated donkey anti-mouse and rhodamine conjugated donkey antigoat antibodies (Jackson Immunoresearch Laboratories) at room temperature for 60 minutes. Specific immunostaining for each antigen was identified in overlapping images generated by analysis of the same section at 488 nm and 568 nm wavelengths, respectively, on a Zeiss LSM410 confocal microscope.

Immunolabeled murine kidney sections showed high background and required an alternative technique. The anti-ECRTP/DEP-1 receptor mAb, ECRTP-Ab1, was directly coupled to FITC. Briefly, ECRTP-Ab1 (0.55 ml of 0.94 mg IgG/ml in 0.1M sodium carbonate buffer, pH 9.0) was conjugated to 0.03 ml FITC solution (Sigma Chemical Co., St. Louis, Mo., 1.0 mg/ml in DMSO) overnight at 4° C. The reaction was stopped by adding ammonium chloride to 50 mM final concentration. Following incubation for 2 hours at 4° C., the mixture was dialyzed exhaustively against phosphate buffered saline to remove unbound FITC. A mouse monoclonal IgG against rat glomerular basement membrane coupled to FITC using the identical protocol was used as a control. Hyink et al., *Am J Physiol* 270:F886–F899 (1996). Acetone fixed sections were blocked with 0.5M ammonium chloride, incubated for 30 min with MoAb-FITC conjugates, washed, and examined by epifluorescence microscopy. In some additional control experiments, the anti-DEP-FITC conjugate was mixed with a molar excess of the immunization peptide before incubation with the sections.
Immunoblots and Immunocytochemistry of Human Endothelial Cell Lines Human endothelial cells grown in 60 mm dishes were lysed at confluency in 0.5 ml of lysis buffer (20 mM TrisCl pH7.5, 50 mM NaCl, 1 mM EDTA, 0.5% Triton X-100, 0.5% SDS, 0.5% deoxycholate, 2 μg/ml aprotinin, 1 μg/ml leupeptin, 1 mM phenylmethylsulfonylfluoride) on ice for 30 minutes. Cleared lysate protein, 150 μg, was incubated with 10 μg/ml of affinity purified rabbit ECRTP/DEP-1 receptor antibody or rabbit IgG (Sigma) at 4° C. for 4 hours, and immunoprecipitates were recovered using Protein-a Sepharose (Sigma). SDS-PAGE, and immunoblotting procedures were carried out as described above. Endothelial cells were grown on uncoated glass coverslips (Fisher), then fixed with 50% methanol for 10 min at 4° C. Coverslips were washed with PBS, blocked with 5% goat serum for 30 min at room temperature, incubated with ECRTPAb-2 monoclonal antibody (10 μg/ml) or VE cadherin monoclonal antibody (2 μg/ml, Transduction Laboratory) for 60 min, washed, then incubated with biotinylated goat anti-mouse IgG (Vector) for 60 min, washed, and finally incubated with fluorescein conjugated (FITC) streptavidin (4 μg/ml, Pierce) for 30 min. Coverslips were mounted and analyzed by confocal microscopy (Zeiss LSM410).
Calcium Chelation to Disrupt Inter-endothelial Cadherin Complexes Confluent HMEC-1 cells grown on glass coverslips in DMEM media supplemented with 15% fetal bovine serum were exposed to addition of EGTA (ethylene glycol-bis(b-aminoethylether)-N,N,N',N',-tetraacetic acid, Sigma) to reach a final concentration of 5 mM. Cells were incubated for an additional 20 min, then fixed with 50% methanol at 4° C. for 10 min, washed with phosphate buffered saline, and stained with monoclonal ECRTP/DEP-1 receptor antibody (10 µg/ml) or VE cadherin monoclonal antibody (2 µg/ml, Transduction Laboratories), as described above.

RESULTS

Figure 1B:
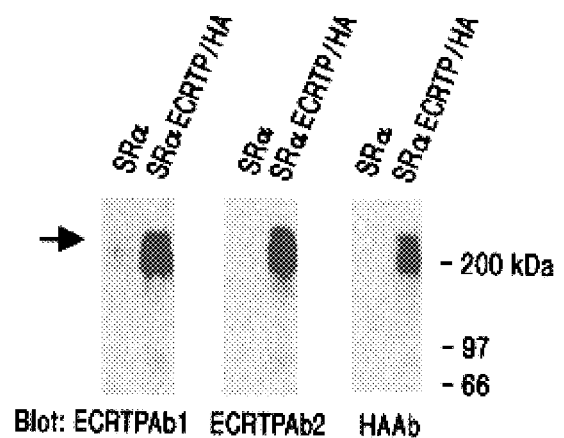
FIG. 1B is an autoradiograph depicting MDCK cells cultured in 100 mm dishes were transfected with 14 μg of empty pSRa vector (SRa) or pSRa-ECRTP/DEP-1/HA (SRa-ECRTP/HA) expression constructs and harvested at 48 hours after transfection. Membrane receptor proteins were recovered by WGA lectin-conjugated agarose from 150 μg of lysate protein. Lectin-adsorbed, eluted proteins were subjected to 7% SDS-PAGE, transferred to a PVDF membrane and probed with ECRTPAb-1, ECRTPAb-2, or anti-HA (HAAb) monoclonal antibodies, as indicated.

Monoclonal antibodies recognize recombinant and expressed ECRTP/DEP-1 receptor. Recombinant fusion proteins representing either ectodomain (Ec) or cytoplasmic domain (Cy) ECRTP/DEP-1 receptor sequences were expressed in bacteria and used to immunize rabbits and/or mice. Shown in FIG. 1A, monoclonal antibodies, ECRTPAb-1 and ECRTPAb-2, specifically identify the ectodomain but not the cytoplasmic domain recombinant proteins. To ascertain whether these antibodies recognize the full length protein expressed in mammalian cells, MDCK cells were transiently transfected with either an empty expression plasmid (SRa) or one driving expression of a full length ECRTP/DEP-1 receptor tagged on the carboxy terminus with a hemagglutinin epitope (SRa DEP-1/HA). Cell lysates from transfected cells were immunoprecipitated using the epitope-specific monoclonal anti-HA antibody, then probed with the antibodies indicated, including ECRTPAb-1 and ECRTPAb-2 (FIG. 1B). Both recognized the 220 kDa HA-tagged ECRTP/DEP-1.

Figure 1C:
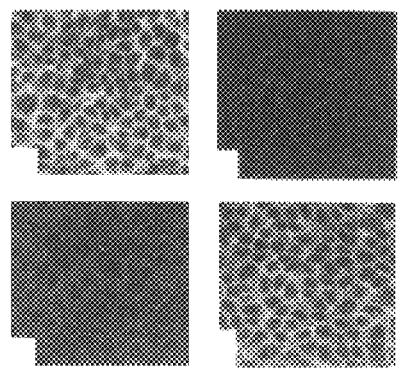
FIG. 1C is a series of photographs depicting MDCK cells stably transfected with the pSRa-ECRTP/DEP-1/HA plasmid were fixed with cold methanol and stained with ECRTPAb-2 (panels a, c & d) or a class matched control antibody (panel b). ECRTPAb-2 labeled lateral borders of cells in contact. Preincubation of ECRTPAb-2 with 50 μg of recombinant immunogen (Ec) blocked this staining (panel c), while an irrelevant recombinant protein (Cy) did not (panel d).

Finally, capacity of the monoclonal antibodies to specifically recognize the ECRTP/DEP-1 receptor expressed in intact cells was assessed using MDCK cells stably trasfected with ECRTP/DEP-1 receptor. Indirect epifluorescence staining with ECRTPAb-2 localized ECRTP/DEP-1 receptor to lateral cell membranes (FIG. 1C, Panel a), a finding confirmed in confocal Z plane sections of MDCK cells grown to confluence on permeable membrane supports. Competition with the immunizing peptide (Ec) blocked immunostaining (FIG. 1C, Panel c) while the irrelevant cytoplasmic domain fusion peptide (Cy) did not (FIG. 1C, Panel d).

ECRTP/DEP-1 receptor immunoreactivity localizes to endothelial cells of glomerular capillaries, peritubular capillaries and renal arteries. To determine the distribution of ECRTP/DEP-1 receptor in mature mammalian kidney, indirect or direct immunofluorescence staining experiments were conducted on frozen sections from human and mouse sources. Shown in FIG. 2, ECRTP-Ab2 immunolocalizes ECRTP/DEP-1 receptor expression to arterial, glomerular and peritubular capillaries, and in particular, to the endothelial cells in these sites. Higher magnification frames show predominant ECRTP/DEP-1 receptor labeling along the luminal membranes of endothelial cells, at least in the arterial sites where endothelial membrane definition is most reliable (FIG. 3).

The punctate characteristic of the staining in the glomerular microcirculation led to the evaluation of whether ECRTP/DEP-1 receptor was engaged in inter-endothelial junctional complexes. In double labeling studies using ECRTP-Ab1 and VE-cadherin antibodies, some overlap was evident (FIG. 3). In addition to the luminal endothelial membrane staining, a regional accumulation of ECRTP/DEP-1 was evident at points of inter-endothelial contact, overlapping, but not limited, to the endothelial junctional complexes that include VE cadherin. Lampugnani et al., *J Cell Biol* 129:203–217 (1995) This pattern was evident in both arterial and peritubular capillaries. In extra-renal sites, capillary and large vessel endothelial cells of brain, lung, liver and spleen was identified and endocardial staining were also apparent.

Figure 4A:
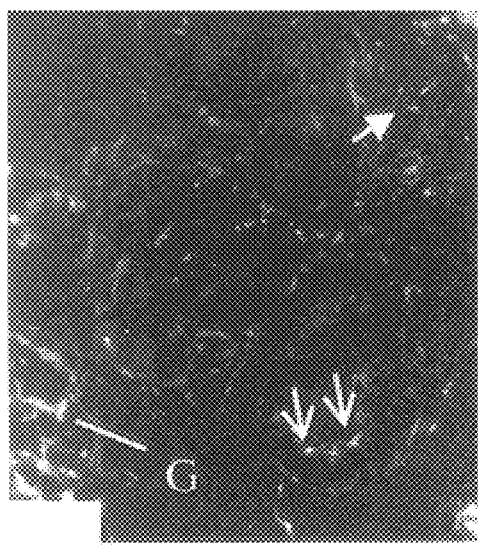
FIG. 4 is a series of photographs depicting ECRTP/DEP-1 receptor expression in developing murine glomeruli. Cryostat kidney sections of embryonic day 14 (A), day 16 (B), postnatal day 6 (C) and adult mice (D) were immunolabeled with ECRTPAb-1 as described in the Methods of Example 1. In panels A & B; ECRTPAb-1 binds to cells dispersed in the mesenchymal area (arrow), to endothelial precursor cells (arrowhead) migrating to the vascular cleft of comma-shaped glomeruli and to endothelium of capillary stage glomeruli (G). In panels C & D, ECRTPAb-1 preferentially labels endothelial cells of the glomerulus (G), artery (A) and peritubular capillaries (arrow) in mature kidney. (Original magnification; A)×400; B)×200; C)×200; and D)×350.
Figure 4B:
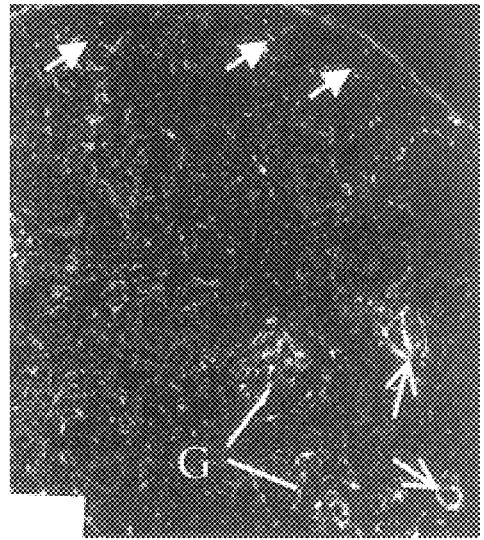

Based on the prominent ECRTP/DEP-1 receptor expression in vascular endothelium of mature kidney, temporal and spatial expression of this receptor during renal vascular development in mouse embryos was evaluated. Shown in FIG. 4, ECRTPAb-1 binds as an antigen, its murine ECRTP/DEP-1 receptor, based on its similar pattern of staining is mature murine and human kidneys, and based on the effect of the recombinant human immunogen (Ec) to block staining of the mouse tissue. In developing mouse kidneys at E14, E16, and postnatal day 6, (FIGS. 4A–C) conjugates of ECRTP-Ab1-FITC displayed a pattern of immunoreactivity that was strikingly similar to the pattern observed previously using antibodies against the VEGF receptor, flk-1, and the EphB1/ephrin-B1 receptor-ligand. Daniel et al., Kidney Int 50:S-73-S-81 (1996). Notably, ECRTP-Ab1-FITC bound to endothelial cells of developing glomeruli and microvessels in the fetal kidney cortex. Small but intense foci of bound antibody were observed on isolated cortical mesenchymal cells believed to be angioblasts (FIGS. 4A & 4B). Within vascular clefts of comma- and S-shaped developing glomeruli, a subpopulation of cells consistent with glomerular endothelial precursors were labeled (FIGS. 4A & 4B).

Figure 3A:
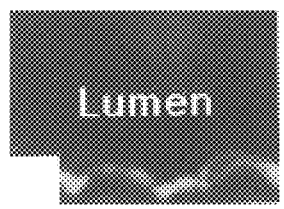
FIG. 3 depicts confocal localization of ECRTP/DEP-1 receptorand VE cadherin in human kidney vasculature. Acetone fixed kidney sections were simultaneously labeled with ECRTPAb-1 and a polyclonal goat antibody against VE cadherin. Bound antibodies were detected using fluorescein conjugated anti-mouse (panels A, B, E, F) or rhodamine-conjugated anti-goat (panels C, D, E, F) Ig antibodies. ECRTPAb-1 (green) staining distributed over the entire endothelial membrane in large artery and glomerular capillaries (A, B) while VE cadherin labeling (red) is restricted to endothelial junctions (C, D). Overlapping confocal images demonstrated co localization of ECRTP with VE cadherin at inter-endothelial junctions. (magnification×600).
Figure 3B:
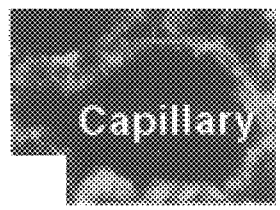
Figure 3C:
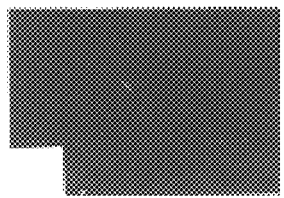
Figure 3D:
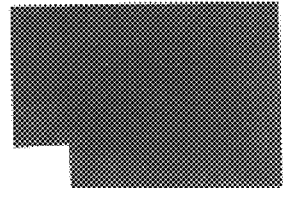
Figure 3E:
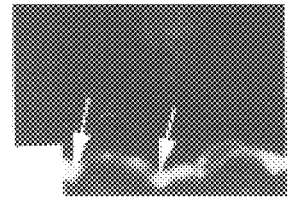
Figure 3F:
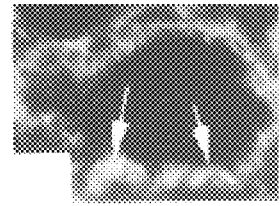
Figure 4C:
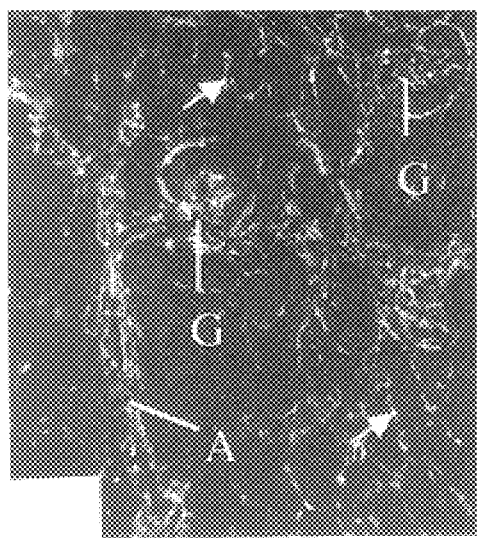
Figure 4D:
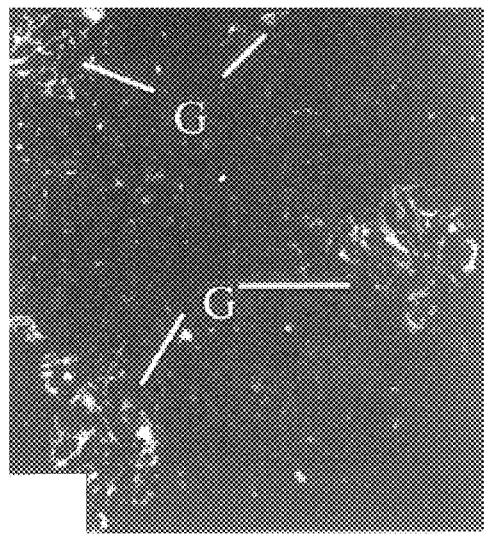

Immunolabeling for ECRTP/DEP-1 receptor on sections of neonatal kidney produced a distinct vascular labeling pattern (FIG. 4C). Arteriolar, glomerular, and peritubular capillary endothelia all labeled intensely (FIG. 3C). Glomerular endothelial cells were also brightly labeled in adult mouse kidney (FIG. 4D), as they were in sections of human kidney. Other cells within the immature and mature kidneys did not bind ECRTP-Ab1-FITC, and sections labeled with control monoclonal IgG-FITC conjugates, or mixtures of ECRTP-Ab1-FITC and the immunization peptide (Ec) showed no staining.

Independent immunoblot and immunofluorescence staining experiments using ECRTP-Ab1 showed high level expression in endothelial cells cultured from a range of different vascular sites, including the HRMEC from which it was cloned, a dermal microvascular endothelial cell line, HMEC-1 (Ades et al., *J Invest Dermatol* 99:683–690 (1992); human umbilical vein endothelial cells; and a HUVEC derived cell line, Eahy926 (Bauer et al., *J Cell Physiol* 153:437–449 (1992). Epitopes recognized by this antibody were not detected in non-endothelial cell lines; including HEK293 cells, glomerular mesangial cells, vascular smooth muscle cells, and P19 embryonic carcinoma cells.

Figure 5A:
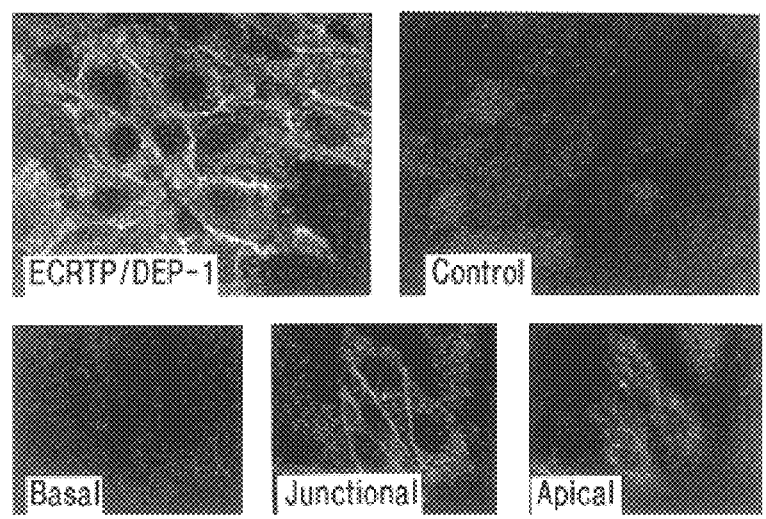
FIG. 5A is a series of photographs depicting Methanol fixed HRMEC cells were labeled with ECRTPAb-2 as described in Methods of Example 1. ECRTP/DEP-1 receptor is distributed between points of inter-endothelial membrane contact and punctate regions of the apical membrane in serial confocal images.
Figure 5B:
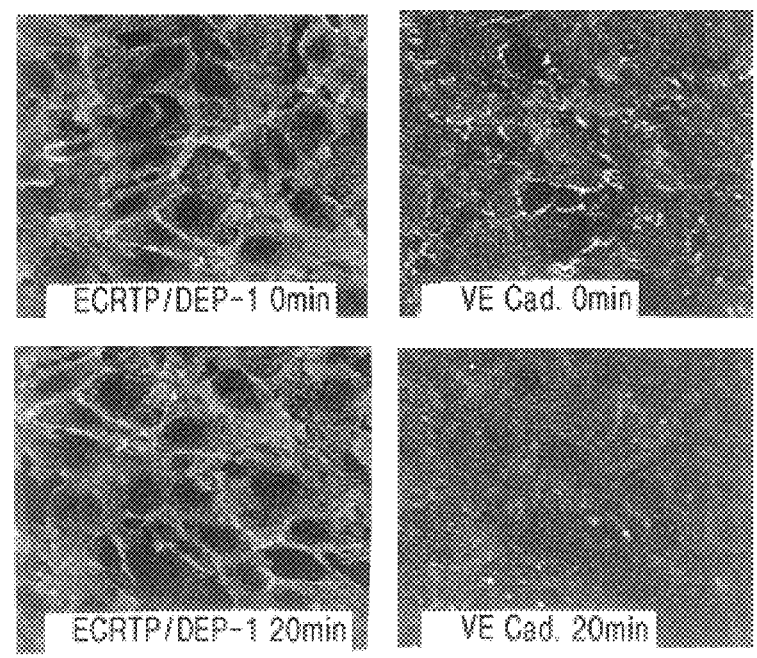
FIG. 5B is a series of photographs depicting HMEC-1 cells were grown to confluency, then incubated with media containing 5 mM EGTA for 0 min (panels a & c) or 20 min (panels b & d), prior to fixation. The distribution of ECRTPAb-2 and VE cadherin labeling was examined as described in Methods of Example 1 at each time. While the distribution of ECRTP/DEP-1 receptor immunoreactivity was not altered in the low $Ca^{2+}$ medium, junctional VE cadherin staining dissipated, consistent with dissociation of VE cadherin junctions and redistribution across the cell membrane.

Shown in FIG. 5 are patterns of ECRTP/DEP-1 receptor localization in human renal microvascular endothelial cells, HRMEC (Panel A), and human dermal microvascular endothelial cells, HMEC (Panel B). Confluent HRMEC cultures displayed prominent staining with ECRTP-Ab2 at points of inter-endothelial contact. In addition, there were punctate accumulations of apical membrane staining in confocal planes capturing the apical surface (Panel A), but not on the basal membrane surface. Endothelial cells plated at sufficiently low density to be isolated from contact with one another did not show the prominent pattern of cell border staining seen in contacting cells. It should be noted that ECRTP-Ab1 did not demonstrate the inter-endothelial localization seen with ECRPT-Ab2, but stained only the subpopulation of receptors evident on the apical surface.

This apparent accumulation of ECRTP/DEP-1 receptor at sites of endothelial cell-cell contact is consistent with the punctate accumulations of staining seen in intact mature vessels, and suggests that a subpopulation of receptors distribute to points of inter-endothelial contact. Thus, the distribution of ECRTP/DEP-1 receptor was compared with that of VE cadherin. Confocal localization of ECRTP/DEP-1 receptor and VE cadherin immunoreactivity in double labeling experiments of confluent HMEC cultures again showed modest overlap of ECRTP/DEP-1 receptor staining with the VE-cadherin localized in inter-endothelial junctions. Similar patterns of colocalization were seen in double labeled sections of human kidney tissue (FIG. 3). Finally, experiments were conducted to ascertain whether the intercellular accumulation of ECRTP/DEP-1 receptor immunoreactivity required the integrity of VE-cadherin interactions. Shown in FIG. 5B, EGTA treatment of the HMEC-1 cells dissociates VE cadherin from the inter-endothelial junctional complexes, but has no apparent effect on ECRTP/DEP-1 receptor localization over the 20–30 minute time period of the experiment. This result suggests that any inter-endothelial junctions that may retain ECRTP/DEP-1 receptor do not require cadherin integrity. Furthermore, these data are consistent with the observations that ECRTP/DEP-1 receptor and VE cadherin overlap, but do not co-localize precisely in intact vessel endothelium (FIG. 3).

DISCUSSION

Several of the observations presented here provide new insights about the ECRTP/DEP-1 receptor tyrosine phosphatase in vascular development and in endothelial cell-cell interactions. The significance of the initial identification of ECRTP/DEP-1 receptor as a transcript expressed in cultured human renal microvascular endothelial cells has been confirmed at several levels. Schoecklmann et al., *J Am Soc Nephrol* 5:730 (1994)(abstract). Cultured HRMEC's express the protein on cell membranes, just as glomerular and peritubular capillaries do in intact kidney tissue. Indeed, capillary and arterial endothelium appear to be the dominant cellular sources of ECRTP/DEP-1 receptor expression in mature human and mouse kidney. In contrast with the previous in situ experiments in rat kidney kidneys, described in Borges et al., *Circulation Research* 79:570–580 (1996), high level expression were found in glomeruli of both mouse and human.

Careful evaluation of the sites of membrane to which ECRTP/DEP-1 receptor distributes has shown prominent apical membrane staining in arterial endothelium in addition to the inter-endothelial membrane staining that appears responsible for the somewhat granular staining pattern in the glomerular capillaries. The lateral cell membrane distribution of ECRTP/DEP-1 receptor in the artificial MDCK epithelial cell system and in contacting cultured HRMEC (FIG. 5), led to the formally evaluation of the relationship of lateral ECRTP/DEP-1 membrane accumulation with VE cadherin complex integrity. The in situ overlap of ECRTP/DEP-1 receptorand VE cadherin immunostaining is modest (FIG. 3), and is restricted to very focal regions of inter-endothelial contact in some, but not all junctional complexes. As ECRTP/DEP-1 receptor lateral membrane distribution is maintained in cultured endothelial cells in which VE cadherin complexes have been dissociated by calcium chelation, it is concluded that there is neither anatomical co-localization nor functional correlation of ECRTP/DEP-1 receptor distribution with maintenance of inter-endothelial complexes. These findings, however, cannot exclude the possibility that lateral ECRTP/DEP-1 membrane distribution may function to establish conditions permissive to assembly of inter-endothelial complexes containing VE cadherin.

Alternatively, the lateral membrane distribution may reflect interaction of the ECRTP/DEP-1 receptor extracellular domain with a putative ligand expressed on contacting membranes that is capable of redistributing receptors or stabilizing them in ligand-receptor complexes created through juxtacrine engagement. Certainly there is available evidence that membrane associated receptor tyrosine phosphatase activity is increased in cultured cells, including endothelial cells, that are in close contact. Pallen and Tong, *Proc Natl Acad Sci USA* 88:6996–7000 (1991); Batt et al., *J Biol Chem* 273:3408–3414 (1998). In the culture systems presented in this Example, an increase in ECRTP/DEP-1 activity that correlates with cell density and with cell-density mediated growth arrest has been demonstrated.

The apical membrane distribution of ECRTP/DEP-1 receptor in arterial and apparently in capillary endothelium is intriguing, particularly in the context of data showing that platelets and all hematopoietic lineages express the ECRTP/DEP-1 receptor. Palou et al., *Immunol Lett* 57:101–103 (1997). Homophilic interactions between ECRTP/DEP-1 receptors of endothelial cells and circulating cells that may encounter them on luminal membranes of intact vessels suggest that it is likely that regulatory factors, or co-receptors on each of the engaging cells are important in modulating any downstream responses.

Finally, the data assessing the developmental pattern of ECRTP/DEP-1 receptor expression on cells that contribute to assembly of the glomerular capillary network offers insight about roles for this receptor in this coordinated process. Receptor tyrosine phosphatases of the ECRTP/DEP-1 receptor subclass, including DPTP10D, have been assigned important roles in the targeting of neurons to correct destinations during development. Desai et al., *Cell* 84:599–609 (1996). Previous reports have identified expression in hematopoietic progenitors, including erythroid, lymphoid and myeloid series lineages. Palou et al., *Immunol Lett.* 57:101–103 (1997). With the accumulating evidence that hemangioblasts serve as common precursors of both hematopoietic and vascular endothelial lineages, it now appears that ECRTP/DEP-1 receptor expression is initiated early in the ontogeny of these precursors. Furthermore, it appears that ECRTP/DEP-1 can function to promote differentiation of erythroid lineage cells that express it. Kumet et al., *J Biol Chem.* 271:30916–30921 (1996).

EXAMPLE 2

ECRTP/DEP-1 Mediates Signals for Endothelial Growth Arrest and Migration Inhibition Powerful endogenous inhibitors of angiogenesis, such as thrombospondin, angiostatin and endostatin, inhibit the proliferation and migration of cultured endothelial cells in vitro. Such angiogenesis inhibitory controls appear to signal arrest of endothelial growth and migration by engaging endothelial surface receptors. One of the most powerful growth inhibitory signals for cultured endothelial cells is imposed by cell-cell contact, which is described in the art as "density mediated growth arrest" or "contact mediated growth arrest". High level expression of the receptor tyrosine phosphatase, ECRTP/DEP-1, at inter-endothelial contacts in microvascular and large vessel endothelium of human kidney and other organs is described in Example 1.

In this Example, the ECRTP/DEP-1 receptor has been determined to mediate endothelial growth and migration arrest signals. The ECRTP/DEP-1 receptor is catalytically activated in conjunction with cell-cell contact. Transient overexpression offull length ECRTP/DEP-1 receptor arrests endothelial growth and migration. Bivalent forms of a monoclonal antibody, ECRTPAb-1, that binds the ECRTP/

DEP-1 receptor ectodomain inhibits endothelial proliferation and migration, while Fab fragments are inactive. This antibody imposes inhibition on corneal angiogenic responses in a mouse system. These findings indicate that the ECRTP/DEP-1 receptor signals endothelial growth and migration arrest upon engagement of its ligand on the surfaces of contacting endothelial cells, and that surrogate activators, or modulators, of endothelial growth arrest signals are viable candidates for angiogenesis inhibitors.

METHODS

Cell Culture

Primary human renal microvascular endothelial cells, HRMEC, were isolated, cultured, and used at third or fourth passage after thawing, as described in Martin etal., In Vitro Cell Dev Biol 33:261–269 (1997). Human dermal microvascular endothelial cells (HMEC-1 cells, CDC) were grown in MCDB131 media (Sigma) containing 15% fetal bovine serum (Hyclone Laboratories, Logan Utah, USA), 10 ng/ml epidermal growth factor (Collaborative Biomedical Products; Becton Dickinson, Bedford, Mass.), and 1 μg/ml hydrocortisone (Sigma). Ades et al., J Invest Dermatol 99:683–690 (1992). All growth media were supplemented with 1 mM L-glutamine (GIBCO BRL), 100 units/ml penicillin and 100 μg/ml streptomycin (GIBCO BRL).

Antibodies

Ectodomain (ECRTP/DEP-$1_{ec}$, amino acids 175–536) and catalytic domain (ECRTP/DEP-$1_{cy}$, amino acids 1048–1338) sequences of human ECRTP/DEP-1 (Ostman et al., Proc Natl Acad Sci USA 91:9680–9684 (1994) were subcloned into the pRSET vector (Invitrogen, Carisland, Calif.). Recombinant fusion proteins were expressed in bacteria, purified by Niagarose affinity (Invitrogen), and characterized by SDS-PAGE as greater than 95% homogeneous proteins of 40 and 36 kDa, respectively. Rabbit antiserum to the ECRTP/DEP-$1_{cy}$ protein was generated by repetitive immunization, and was affinity purified, as described in Koenig et al., J Clin Immunol 13:204–211 (1993). Mouse hybridoma antibody ECRTPAb-1 was obtained following immunization with ECRTP/DEP-$1_{ec}$ protein by intraperitoneal immunization, fusion with SP2-0 cells, ELISA screening, selection, expansion and purification by affinity chromatography on protein A-agarose (Sigma).

Assays for ECRTP/DEP-1 receptor Abundance and Tyrosine Phosphatase Activity

Cells plated at the densities and harvested at the times indicated in the Figure Descriptions were washed repeatedly with iced phosphate buffered saline before in situ addition of 2 ml of buffer containing 50 mM Hepes (pH 7.5), 50 mM NaCl, 5 mM EDTA, 1 mM PMSF, 1 mM β-mercaptoethanol, 1% Triton X-100. Detergent solubilized cells were incubated for 15 min at 4° C. and insoluble material was removed by repeated microcentrifugation (two times) at 13,000×g, 10 min, 4° C. Proteins in solubilized fractions were quantitated using a modified BCA assay (Pierce). In some experiments, batch adsorption and elution from triticum vulgaris lectin (WGA) conjugated to agarose (Sigma) was conducted as described in Stein et al., J Biol Chem 271:23588–23593 (1996). Final elution for fractions subjected to phosphatase assays was in buffer containing 25 mM imidazole (pH 7.2), 0.1 mg/ml bovine albumin, 10 mM dithiothreitol (phosphatase assay buffer), plus 3 mM N,N', N" triacetylchitotriose (Sigma).

$^{32}$P-labeled, phosphorylated substrate (Raytide) was prepared by the manufacturer's recommendations as described (Oncogene Sciences) to achieve specific activities of (dpm/fmol). Phosphatase activity in lectin purified fractions was assayed in triplicate at 30° C. for times indicated in the Figure Descriptions in 200 μl volumes of phosphatase buffer using 300 ng/ml substrate in the presence or absence of $Na_3VO_4$, as described. Released phosphate was quantitated by scintillation counting and data are expressed as mean cpm+/−SEM. Assays were linear over 1–10 min periods.

Figure 8A:
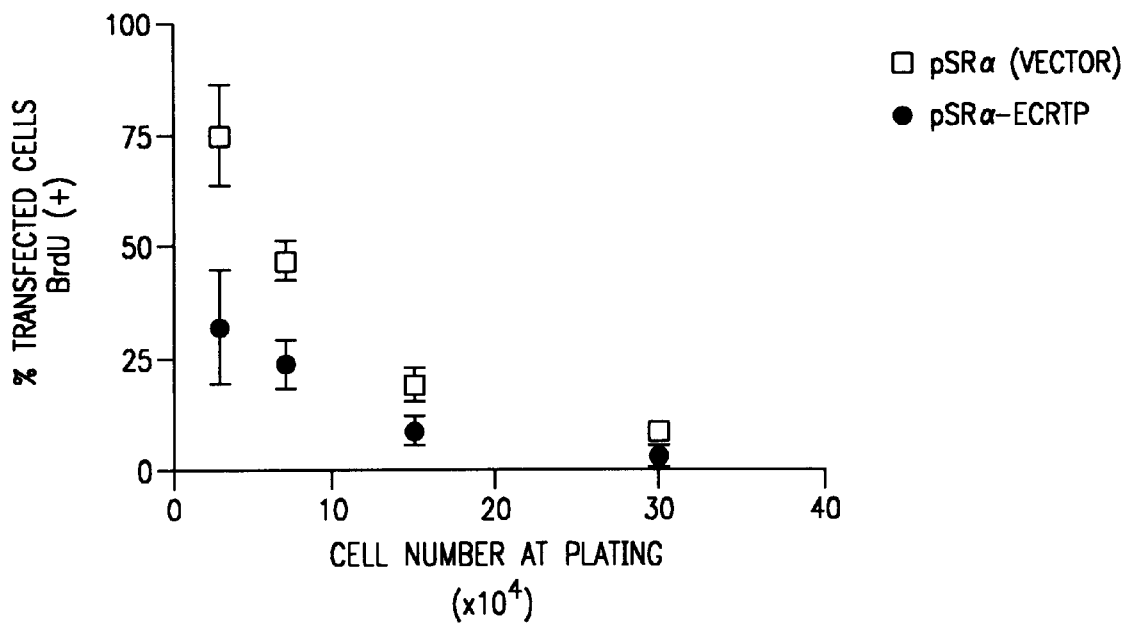
FIG. 8A is a graph showing transient transfection of HMREC with ECRTP/DEP-1 cDNA imposes a growth inhibition at low cell densities. Approximately $3 \times 10^5$ HRMEC were cotransfected with 1.7 µg pSRα (vector control) or HA epitope tagged (hemagglutinin) pSRα-ECRTP/DEP-1 (pSRα-ECRTP), as indicated, and 0.4 µg pEGFP (Clontech) to permit scoring of BrdU labeling of transfected cells, as described in Methods of Example 2. At 24 hours, transfected cells were replated on p35 dishes in the numbers indicated. Thirty six hours later, S phase cells were labeled for 30 min with BrdU, as described in Methods of Example 2, and +GFP positive cells were scored for BrdU incorporation. Data represent means+/−SEM for quadruplicate determinations.

For determination of ECRTP/DEP-1 receptor activity and abundance (FIG. 8) HRMEC cells were plated at cell densities indicated in the Figure Descriptions. At 36 hours after plating, a subset of cells, as indicated, was treated for 10 min with pervanadate (1 mM $H_2O_2$+1 mM $Na_3VO_4$), then cells were lysed in buffer containing 50 mM HEPES/pH7.5, 150 mM NaCl, 5 mM EDTA, 1% Triton X-100, 0.1 mM, 5 μg/ml aprotinin, 1 μg/ml leupeptin, 1 mM PMSF, clarified by centrifugation and equivalent lysate proteins (150 μg) were immunoprecipitated by incubation with affinity-purified monospecific ECRTP/DEP-1 receptor rabbit antibody (12.5 μg/ml) overnight at 4° C., and collected on protein A-sepharose (Sigma).

The washed immunocomplexes were assayed for PTP activity with p-nitrophenylphosphate, pNPP (Sigma) as previously described in Wang, Y. and Pallen, C. J., J Biol Chem 267:16696–16702 (1992). Briefly, the immunocomplexes were incubated with reaction mixture (50 mM sodium acetate/pH 5.5, 0.5 mg/ml bovine albumin, 0.5 mM DTT, 5 mM pNPP) at 30° C. for 30 min in the absence or presence of 1 mM $Na_3VO_4$. Reactions were stopped by addition of 2N NaOH, and the absorbance at 410 nm was measured.

For quantification of ECRTP/DEP-1 receptor abundance, immunoprecipitated fractions were also resolved by 7% SDS-PAGE under reducing conditions, transferred to PVDF membranes (Immobilon-P, Millipore), and blocked in 5% non-fat dry milk in Tris-buffered saline (50 mM Tris/HCl pH7.5, 137 mM NaCl) containing 0.2% Tween 20 (TBST) overnight at 4° C. Blots were incubated with ECRTPAb1 (10 μg/ml) or phosphotyrosine monoclonal antibody, 4G10, (1.0 μg/ml, Upstate Biotechnology) and bound antibodies detected with horseradish peroxidase-conjugated rabbit antimouse IgG antibody (Boehringer) and a chemiluminescent reagent (ECL; Amersham Corp).

Proliferation Assays

In initial assays of HRMEC proliferation (FIG. 6), cells were plated at the indicated density, harvested at the indicated times and counted in quintriplicate. Data represent means±SEM. In other experiments (FIGS. 8 and 9), HMEC-1 cells were grown on a 35 mm diameter dish (Falcon) and cotransfected with ECRTP/DEP-1 receptor expression plasmids (either parent vector, pSRα, or pSRα-ECRTP/DEP-⅓×HA, driving high level expression of a carboxyterminal hemagglutinin (HA) epitope tagged human ECRTP/DEP-1, 1.8 μg) and a green fluorescence protein expression plasmid (pEGFP, Clontech, 0.4 μg). An adenovirus-assisted lipofectamine procedure that transfects 40–50% of HMEC-1 cells under these conditions was used, as is also described in Example 1. Transfected cells were harvested 48 h after transfection and replated on glass coverslips in individual wells of a 12 well plate at densities indicated in the Figure Descriptions (range 2–10×10$^4$), to achieve attached cell confluencies of 20–90+%). Proliferating cells were labeled by addition of 10 μM 5-Bromo-2'-deoxy-uridine (BrdU) to culture media for 30 min at 70 hours after transfection. BrdU incorporation was immunocytochemically detected using a monoclonal BrdU antibody and rhodamine-conjugated anti-mouse IgG, according to manufacturer's protocol (Boehringer Mannheim). The cells of at least five independent fields were observed under epifluorescence microscopy (Nikon ECLIPSE E600) and the frequency of BrdU labeling in GFP positive cells was scored.

Planar Endothelial Migration Assay

A planar endothelial migration assay was developed to assess the rate of endothelial closure of circular "wounds" of 300–500µ diameter. A rotating silicon-tipped bit attached to a drill press was used to generate 3–5 "wounds" in confluent endothelial monolayers within individual wells of multi-well plates. At the time of "wounding", medium in individual wells were supplemented with agents at concentrations indicated in the Figure Descriptions. Residual areas of individual wounds in photomicroscopic images captured at the indicated times (4 & 8 hours) were quantitated using a Bioquant (Nashville, Tenn.) software package calibrated to a Nikon Diaphot microscope. Expressed in this manner, the rates of wound closure are remarkably linear, with linear regression $r^2$ values $\geq 0.985$. Each data point displayed here represent the mean±SEM of three or more individual determinations from the same well. Each experiment described is representative of findings from three or more independent observations.

In situ Transfection Assay for Migration

Confluent HMEC-1 cells grown on 6 well culture plate were transfected with 2.2 µg of expression plasmids, pSRα ECRTP/DEP-⅓xHA, or pSRα-EphB⅓xHA (Stein et al., *Genes Dev* 12:667–678 (1998)) and circular wounds were prepared at 48 hours after transfection as described above. When the wounds were almost closed (12 h after wounding), monolayers were fixed with 2% paraformaldehyde for 20 min, washed with phosphate buffered saline, permeabilized with 0.02% saponin for 60 min, blocked with 5% goat serum and incubated with 5 µg/ml of monoclonal HA antibody, 12CA5, (Babco) for 60 min. Coverslips were then washed with phosphate buffered saline, incubated with biotinylated goat anti-mouse IgG (Vector Laboratories, 7.5 µg/ml) for 60 min, washed, incubated with HRP conjugated avidin-biotin complexes (Vector Laboratories) for 30 min and finally developed using 6 mg/ml of 3,3'-diaminobenzidine (Sigma).

Cornea Pocket Angiogenesis Assay

Agents to be tested for angiogenic or anti-angiogenic activity were immobilized in a slow release form in an inert hydron pellet of approximately 0.2 µl volume, as described in Kenyon, Voest, et al. (1996). That pellet is implanted into the corneal epithelium of an anesthetized C57BL mice in a pocket created by micro-dissection. Over a 5 to 7 day period angiogenic factors stimulate the ingrowth of vessels from the adjacent vascularized corneal limbus. A photographic record is generated using slit lamp photography. The appearance, density and extent of these vessels are evaluated and scored. In some cases the time course of the progression is followed in anesthetized animals, prior to sacrifice. Vessels are evaluated for length, density and the radial surface of the limbus from which they emanate (expressed as clock-face hours).

RESULTS

Figure 6A:
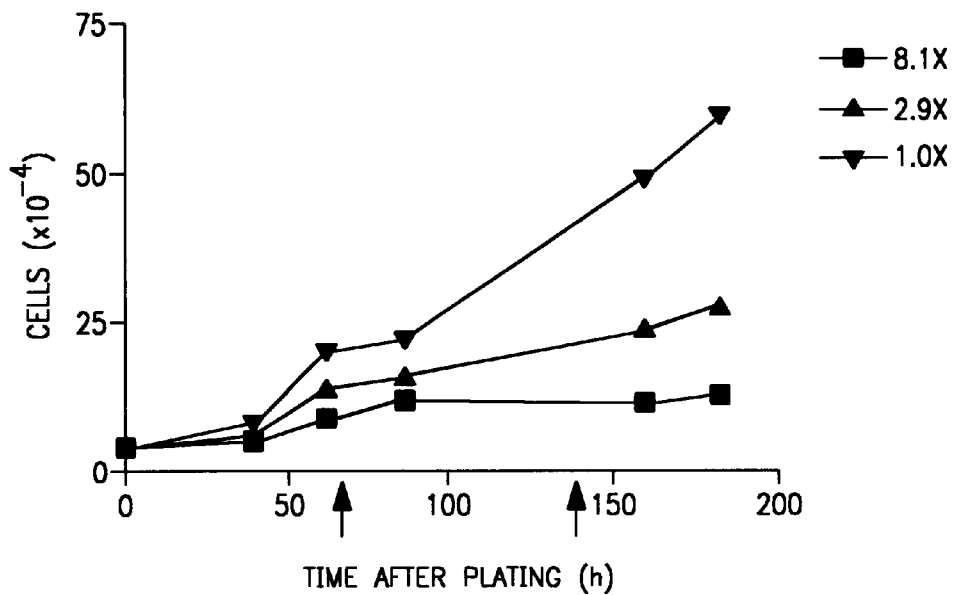
FIG. 6A is a line graph showing identical numbers of human renal microvascular endothelial cells (HRMEC) were plated in growth medium on 100 (1×), 60 (2.9×) or 35 (8.1×) mm diameter plastic dishes, effecting the indicated fold differences in cell density at the time of plating. Medium was replaced with growth medium at points indicated by arrows. Cells were counted in a Coulter counter and means of quadruplicate samples are displayed. Proliferation was arrested in cells at 8.1×density after a single cell doubling, and after approximately 3 doublings in cells plated at 2.9×density.
Figure 6B:
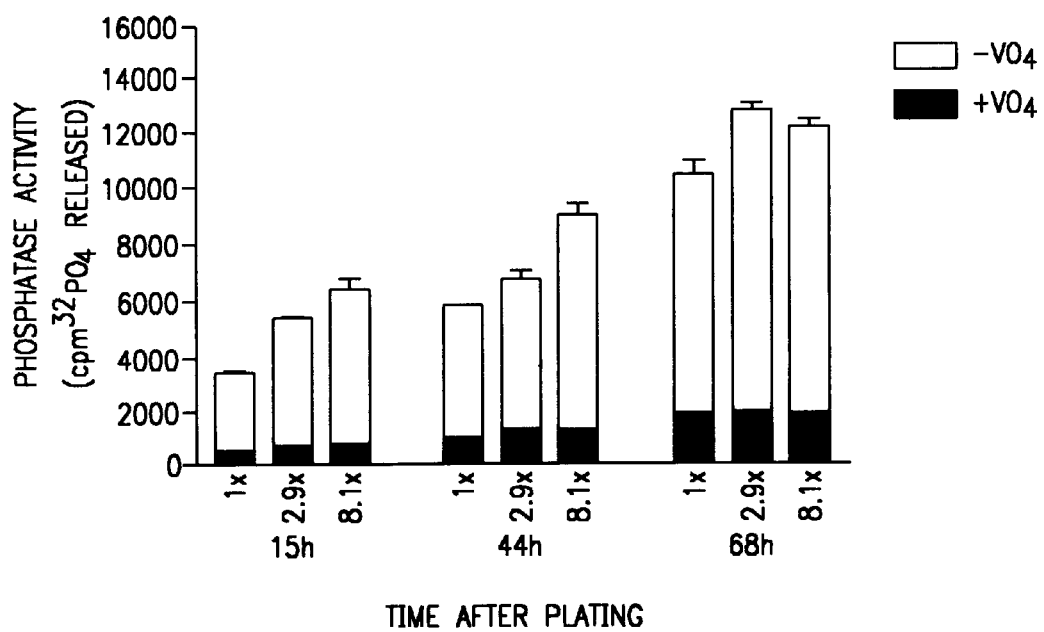
FIG. 6B is a bar graph showing cells plated for the indicated times at the indicated densities were lysed, and receptor tyrosine phosphatase activity, including that attributable to ECRTP/DEP-1 receptor, was recovered by lectin affinity chromatography and assayed as described in Methods of Example 2 in the absence or presence of the tyrosine phosphatase inhibitor, sodium orthovanadate ($VO_4$, 100 μM).

Initial experiments were conducted to establish the cell density (cell number/surface area) at which human renal microvascular endothelial cells (HRMEC) display growth arrest in serum supplemented growth medium. In situ experiments have shown high level expression of ECRTP/DEP-1 receptor in glomerular and extraglomerular microvascular endothelial cells of human kidney, as well as in arteries and a wide range of other tissues. In FIG. 6A, identical numbers of HRMEC were plated on cell culture plates of 9.6, 28.3, or 78.5 cm², representing 1, 2.9, or 8.1 fold the surface area of a 35 mm diameter dish, as indicated. Growth medium was replaced every 3 days. Depending upon passage number, HRMEC reached growth arrest at a density of approximately $1.3–6 \times 10^4$ cells/cm², a response that supercedes responses to maximal growth stimuli. Doubling time under density unrestricted conditions is approximately 44 hours. The established human dermal microvascular endothelial cell line, HMEC-1, similarly displayed density-mediated growth arrest properties.

Increasing fibroblast cell density was previously associated with increases in tyrosine phosphatase activity recovered from membrane-associated fractions. See e.g., Pallen, C. J. and Tong, P. H. *Proc Natl Acad Sci USA* 88:6996–7000 (1991). Among membrane-associated proteins, may surface receptors, including ECRTP/DEP-1, are modified by N-linked glycosylation of the ectodomain region and may be recovered using lectin affinity chromatography. Honda et al., *Blood* 84:4186–4194 (1994). Shown in FIG. 6B, tyrosine phosphatase activity of the *triticum vulgaris* (wheat germ agglutinin, WGA) lectin fraction recovered from identical numbers of HRMEC plated was analyzed for the indicated times at densities determined by the culture dish surface area. As early as 15 hours after plating, marked differences in vanadate-sensitive tyrosine phosphatase activity were evident. Lectin-recovered receptor-associated tyrosine phosphatase activity was 2 fold higher in cells plated at a density sufficient to impose growth arrest (8.1×), compared with those plated at lower density (1×). As cells plated at lower densities (2.9 and 1×) proliferated, increases in activity were seen, eliminating the marked difference. The increased lectin-recovered activity was evident at times anticipating the imposition of proliferation arrest, suggesting that either the prevalence of specific tyrosine phosphatases was increasing, that the activity of pre-existing phosphatases was increased, or that tyrosine phosphatases were being recruited to associate with lectin recovered proteins. The previous report that DEP-1 receptor prevalence increased with increasing cell density lead us to evaluate the activity and distribution of DEP-1. Ostman et al., *Proc Natl Acad Sci USA* 91:9680–9684 (1994).

Figure 7:
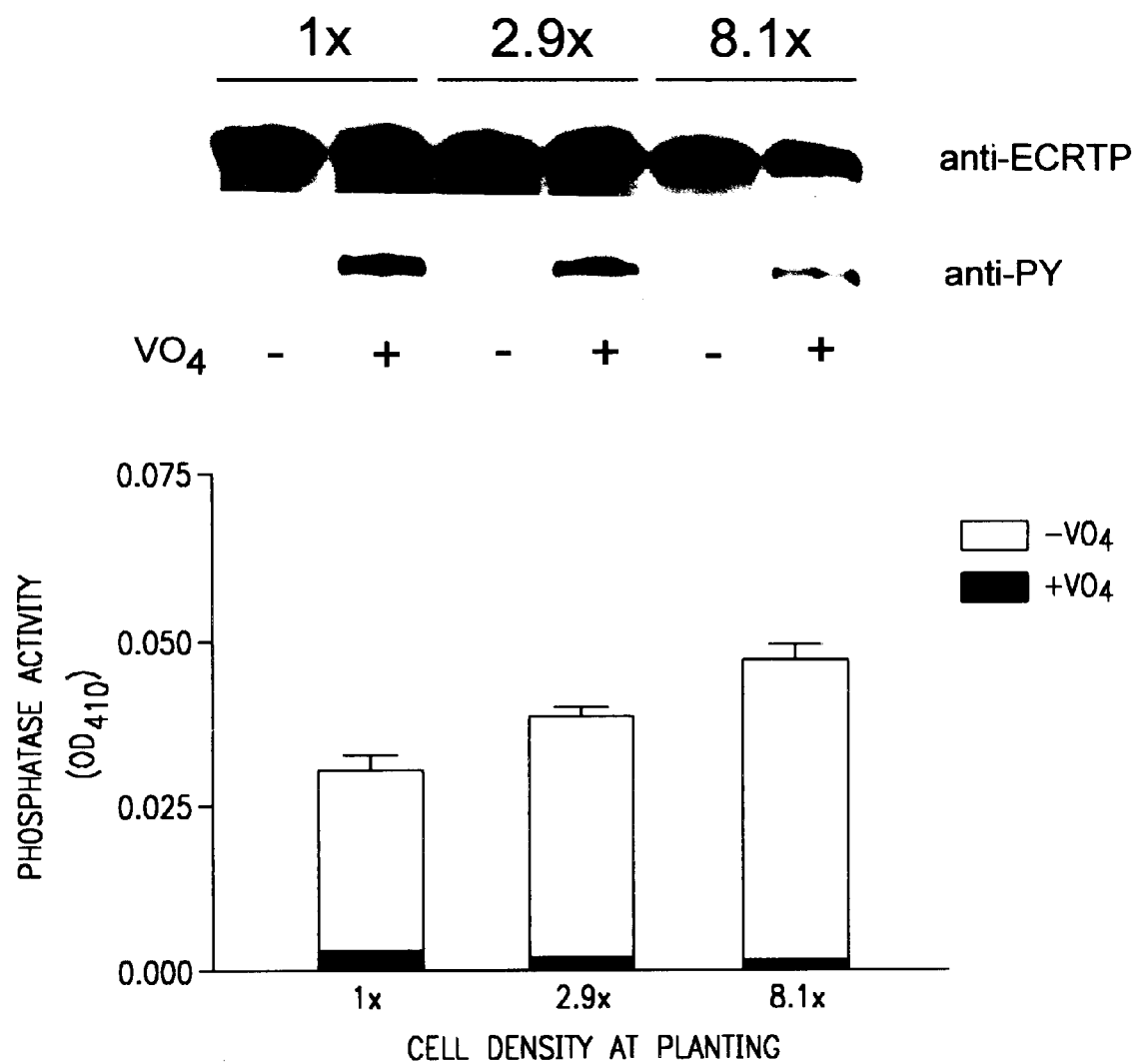
FIG. 7 is an autoradiograph and a bar graph showing that increased cell density imposes increases in activity, but not amount, of immunoprecipitated ECRTP/DEP-1 receptor. Identical numbers of HRMEC were plated as in FIG. 6 at the indicated cell densities. Monospecific affinity purified rabbit polyclonal antibodies were used to immunoprecipitate ECRTP/DEP-1 receptor from cells treated for 10 min immediately before harvest with 1 mM peroxyvanadate ($+VO_4$) or vehicle ($-VO_4$) at 36 hours after plating, as described in Methods of Example 2. Recovered ECRTP/DEP-1 receptor antigen was quantitated by immunoblot with the monospecific antibody and its endogenous phosphotyrosine content assessed by phosphotyrosine immunoblot using the 4G10 monoclonal antibody. Phosphatase activity in immunoprecipitated samples was assayed using pNPP as substrate in the absence ($-VO_4$) or presence ($VO_4$) of sodium orthovanadate, as described. Data are displayed as optical density of the product in triplicate samples+/−SEM.

Shown in FIG. 7, differences in the amount of immunoprecipitated ECRTP/DEP-1 receptor antigen could not be detected when cells plated for 33 hours at different densities were compared. Additional experiments failed to show a change in the ratio of Triton X-100 soluble to insoluble fractions at these densities (not shown). However, 1.8 fold increases in the vanadate-sensitive ECRTP/DEP-1 receptor associated tyrosine phosphatase activity were recovered by immunoprecipitation from cells plated at the highest (8.1×) compared with the lowest (1×) cell density. Shown in the lower panel immunoblot (FIG. 7), immunoprecipitated ECRTP/DEP-1 receptor is itself a tyrosine phosphoprotein in cells pretreated with vanadate. Moreover, the level of intrinsic phosphotyrosine is decreased in the immunoprecipitated ECRTP/DEP-1 receptor recovered from cells plated at high density, correlating with the increased tyrosine phosphatase activity in that fraction. These findings indicate that the abundance of ECRTP/DEP-1 receptor does not change acutely in endothelial cells plated at high density, but that the ECRTP/DEP-1 associated phosphatase activity does increase. Efforts to demonstrate by in gel zymographic phosphatase assays that the increased activity is intrinsic to ECRTP/DEP-1 receptor have not been successful.

To further pursue the possibility that ECRTP/DEP-1 receptor mediates signals capable of arresting endothelial proliferation and migration, HMEC-1 cells were cotransfected with an expression plasmid driving high level expression of an epitope-tagged ECRTP/DEP-1, and with a plasmid driving expression of green fluorescent protein to mark transfected cells. Using adenovirus-assisted transfection method, transfection of 40–50% of HMEC-1 cells that display survival, migration and proliferation properties similar to nontransfected cells was routinely accomplished. Shown in FIG. 8A, high level expression of a full length ECRTP/DEP-1 receptor imposes marked suppression of BrdU incorporation across a range of plating densities of transfected cells when compared with the empty expression vector.

ECRTP/DEP-1 receptor overexpression imposed similar effects upon endothelial migration as those observed with proliferation. Shown in FIG. 9A, HMEC-1 cells transfected with plasmids driving expression of hemagglutinin epitope (HA) tagged versions of either ECRTP/DEP-1/HA or a receptor tyrosine kinase, EphB1/HA, were plated at densities to permit them to rapidly attain a confluent monolayer. A circular "wound" of approximately 500 µm diameter was generated, and migration of transfected and non-transfected cells to close the "wound" was determined after 33 hours, by staining for the expressed protein HA epitope. Unlike cells transfected wiith the EphB1/HA control, ECRTP/DEP-1/HA expressing cells did not migrate to contribute to the wound closure. While forced overexpression of ECRTP/DEP-1 receptor may be informative about the potential for this receptor to affect proliferation or migration, this approach is much less discriminatory than use of high affinity reagents interacting with endogenously expressed ECRTP/DEP-1 receptors. To this end, we screened a panel of monoclonal antibodes we generated against ECRTP/DEP-1 receptor ectodomain sequences for activity.

Figure 8B:
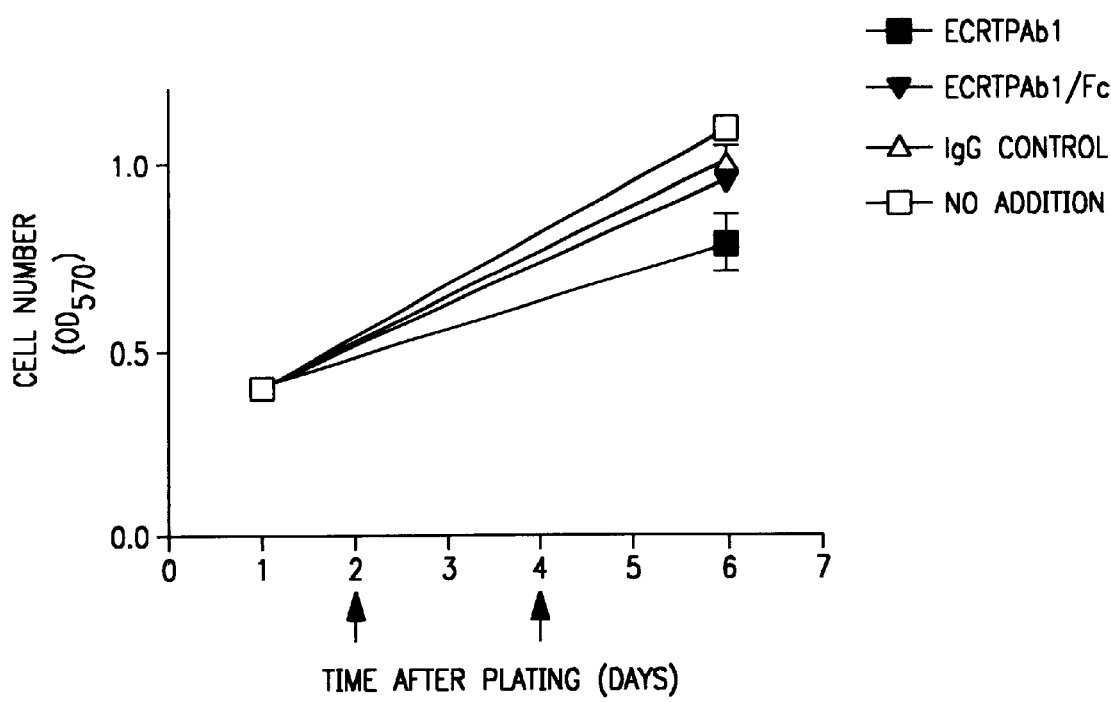
FIG. 8B is a line graph showing that ECRTPAb-1 inhibits endothelial proliferation and migration. HRMEC ($3 \times 10^4$) were plated in p35 dishes at time 0. Growth medium was replaced at 24 h, cells were counted, and either IgG control (10 µg/ml) or ECRTPAb1 (10 µg/ml) antibodies were added. Replicate samples (5) of cells were counted on day 4, and are expressed as means+/−SEM.

Shown in FIG. 8B, bivalent forms of the monoclonal, ECRTPAb1, imposed a marked inhibitory effect on proliferation of HRMEC plated at low density, in spite of repeated growth medium exchanges. Equivalent concentrations of a class matched monoclonal control antibody were inactive. Because oligomerization is a critical determinant of activation of many receptor tyrosine kinases and phosphatases (Weiss, A. and Schlessinger, J., *Cell 94:277–280* (1998)), ECRTPAb1 Fab fragments were prepared to test whether bivalency of the interacting monoclonal was required for activity. Also shown in FIGS. 8B and 8C, equimolar concentrations of the ECRTPAb1 Fab fragments were inactive as growth inhibitors in endothelial cells plated at subconfluent densities in serum-containing growth medium.

Figure 8C:
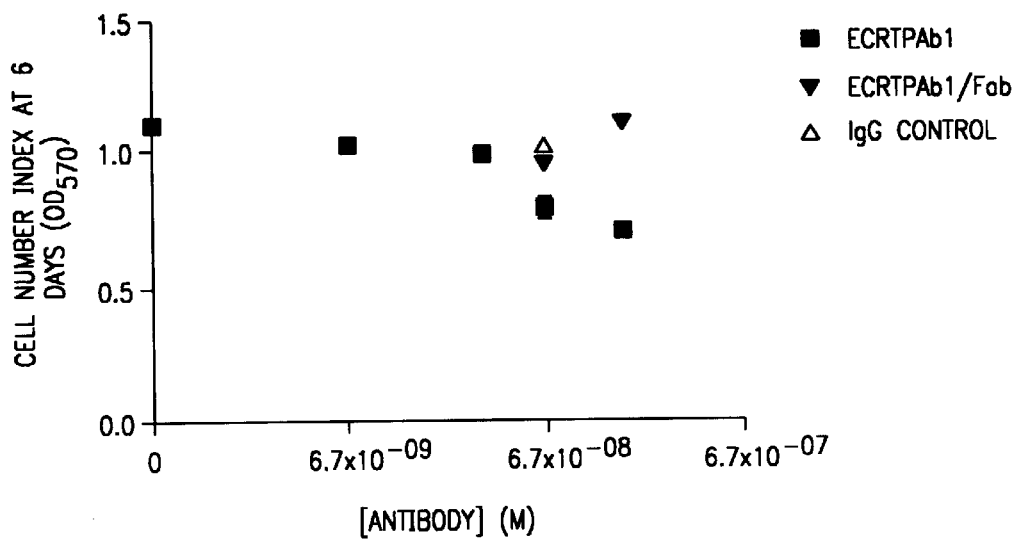
FIG. 8C is a data point plot depicting that as in FIG. 8, equal numbers of HRMEC were plated at time 0, and antibodies or Fab fragments added at the concentrations indicated. Replicate plates were harvested on day 1, to confirm homogeneous plating efficiency in each condition, and on day 6 to assess cell proliferation, respectively. Data points represent mean values of five replicates±SEM.
Figure 9B:
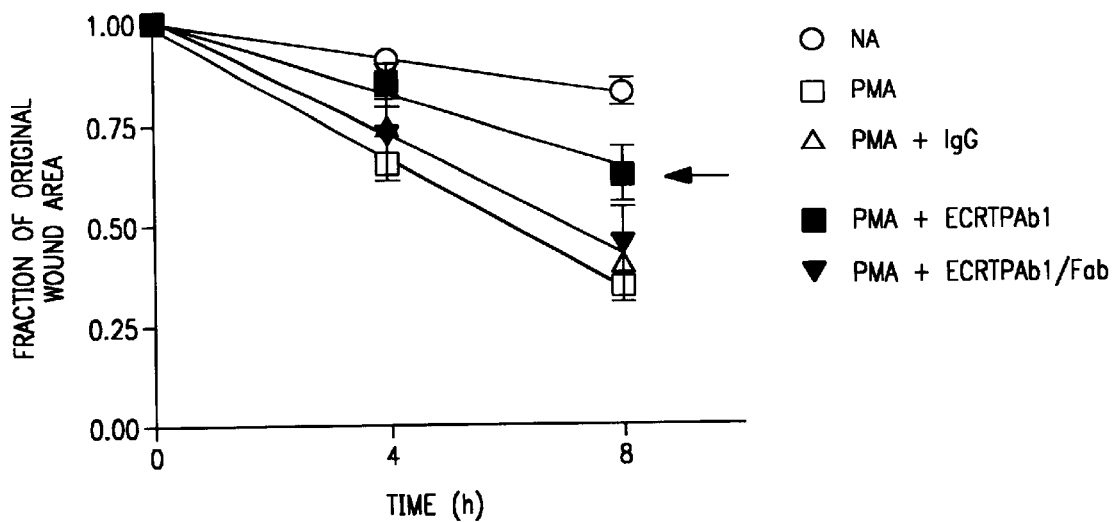
FIG. 9B is a line graph reflecting analysis of 300 to 420 µm diameter "wounds" which were created in HRMEC confluent monolayers at time 0, as medium was exchanged to serum-free medium supplemented by either no addition (NA), or phorbol myristate acetate (20 ng/ml) in the presence of the indicated antibodies or fragments, including a class matched IgG control (IgG, 10 µg/ml), ECRTPAb1 (10 µg/ml), or Fab fragments of ECRTPAb1 (3 µg/ml, molar equivalency). Triplicate wounds were used to generate microscopic images at the indicated times, and the residual "wound" area calculated and expressed as a fraction of the original wound, by an automated capture sequence using Bioquant Image Analysis Software. Each data point represents the mean±SEM of three determinations.
Figure 9A:
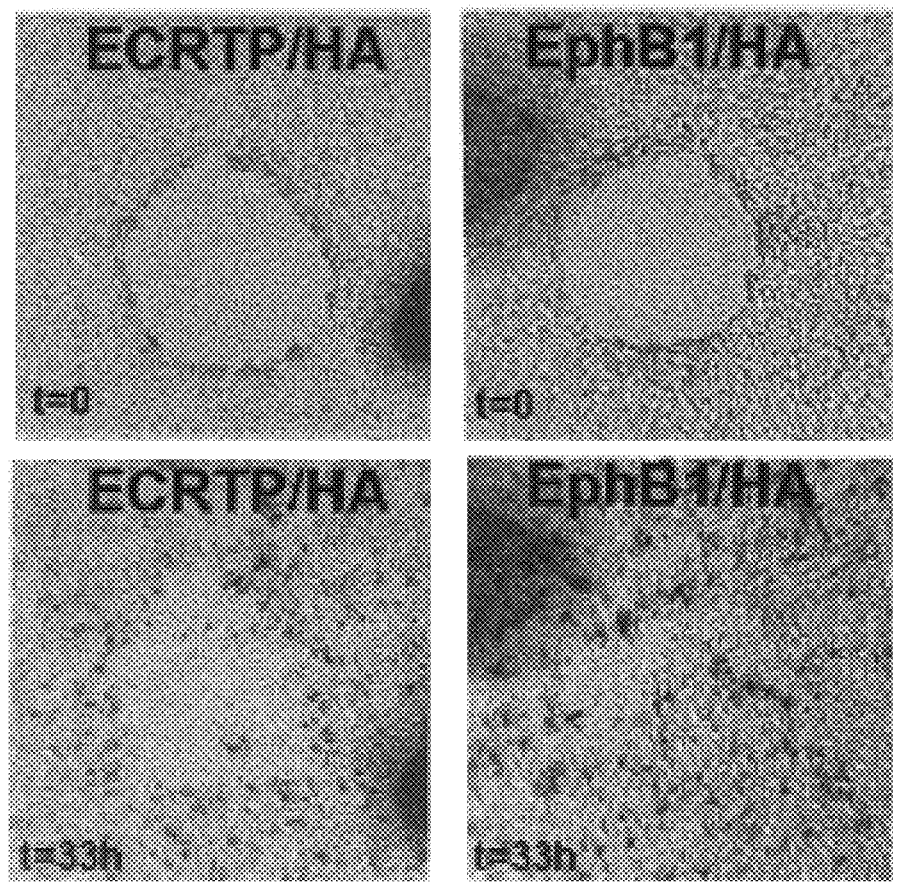
FIG. 9A is a series of photographs depicting monolayers of HRMEC were transiently transfected with plasmid pSRαECRTP/DEP-1/HA, or pSRαEphB1/HA, as indicated. Forty eight hours later, "wounds" were created in the confluent monolayers and permitted to close over the ensuing 30 h. Monolayers were then stained with the monoclonal hemagglutinin antibody, 12CA5, to detect the positions of cells transiently expressing high levels of ECRTP/DEP-1/HA or EphB1/HA, respectively. Only rare ECRTP/DEP-1 overexpressing cells migrated to close the "wound".
Figure 9C:
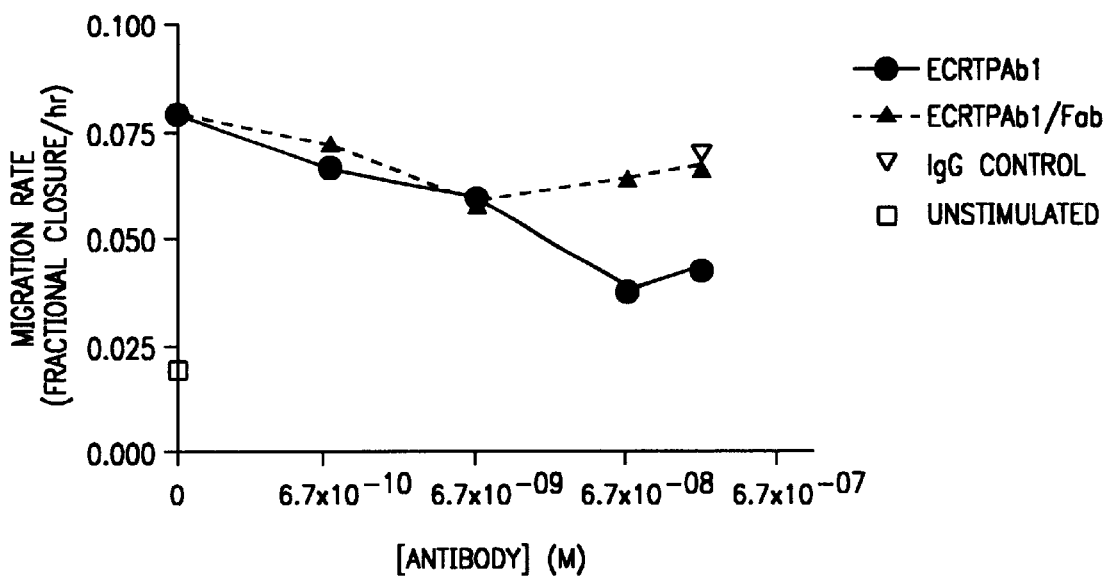
FIG. 9C is a line graph analyzing data produced by the same assay procedure as FIG. 9B. Using the same assay procedure, migration rates were calculated by linear regression of mean values determined in cells exposed to IgG control, ECRTPAb1, or ECRTPAb1/Fab, using three independent time points. $r^2$ values≧0.90 for each data point plotted. The open square □(D) indicates the migration rate for closure of unstimulated cells.

Additional endothelial "wound" closure assays, similar in design to those presented in FIG. 9A, were conducted to evaluate effects of bivalent and monovalent ECRTPAb1 on endothelial migration. Displayed in FIG. 9B are the residual fractions of original wound areas remaining at the times indicated. Phorbol myrisate acetate (PMA) markedly accelerated the rate of migration and wound closure, compared with unstimulated cells in serum-free medium. Bivalent ECRTPAb1 displayed marked activity to inhibit the PMA stimulated migration, while equimolar concentrations of monovalent Fab fragments, and a control monoclonal were inactive. The linear characteristics of time dependent "wound" closure in this assay permitted us to determine relative migration rates for the population, expressed in FIG. 9C as fractional closure/hr. Effective concentrations of bivalent ECRTPAb1 (67 and 200 nM) were similar to those active as inhibitors of proliferation (FIG. 8C).

Figure 10:
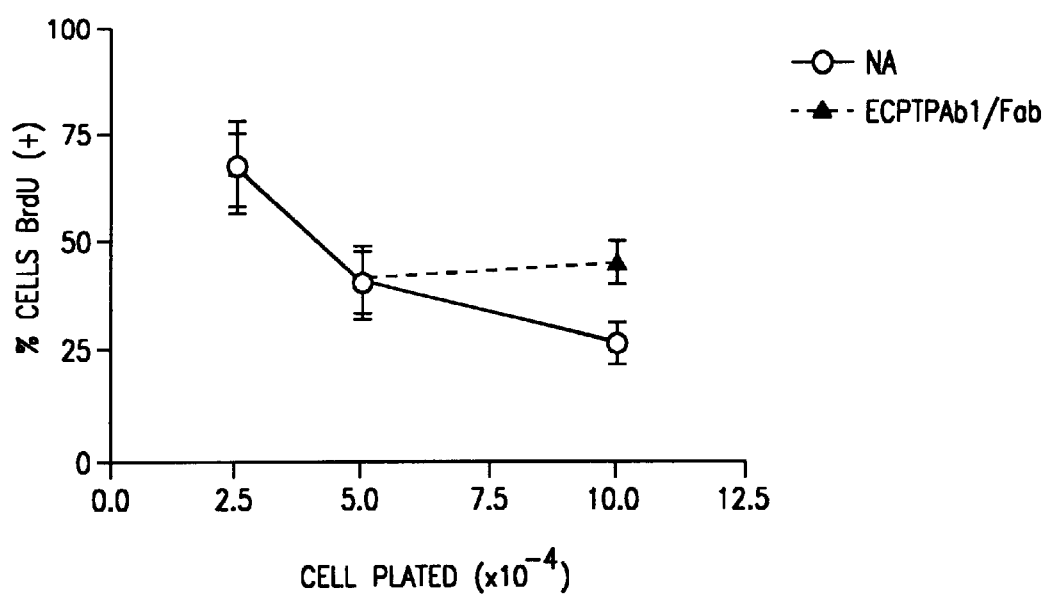
FIG. 10 is line graph depicting that ECRPTAb1 Fab fragments attenuate endothelial density mediated growth arrest. HMEC-1 cells of the indicated numbers were plated in on coverslips in 12 well dishes at time 0 in growth media supplemented by no addition (NA) or ECRTPAb1 (67 nM). Twenty four hours later BrdU staining was assayed as described in Methods of Example 2 and the percentage of BrdU positive cells scored by counting of five independent fields for each condition (greater than 400 cells/point). Data represent means±SEM.

In aggregate, these findings suggested that engagement of endogenous ECRTP/DEP-1 receptors by bivalent antibodies may function like a "surrogate ligand" to emulate responses normally evoked by an endogenous membrane-associated ligand upon cell-cell contact. Since the ECRTPAb1 Fab fragments were inactive as "surrogate ligands" to inhibit migration and proliferation in subconfluent cells, we asked whether they may have activity as antagonists of endogenous ligand engagement of ECRTP/DEP-1 receptor in cells plated at high density. We reasoned that Fab fragments may interrupt endogenous ligand-receptor engagement and subsequent growth arrest signals in cells plated at high density. Shown in FIG. 10, ECRTPAb1 Fab had a marked effect to release cells from the density-imposed inhibition of BrdU uptake that marks S phase entry.

Figure 11:
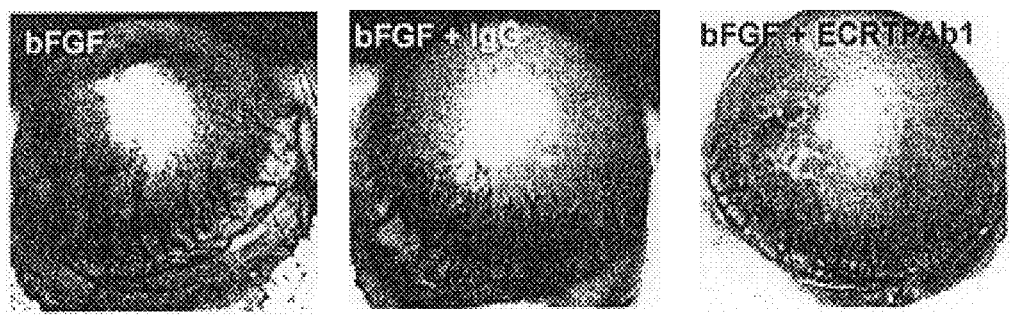
FIG. 11 is a series of photographs depicting that ECRTPAb1 inhibits corneal pocket angiogenesis responses to bFGF. Hydron pellets were impregnated with the angiogenesis stimulant, basic FGF (90 ng), alone, or supplemented with a class matched control monoclonal antibody (IgG, 200 ng) or ECRTPAb1 (200 ng), and placed in a pocket created in the corneal epithelium of anesthetized mice. Five days after implantation, angiogenic responses were scored, and photographed. Representative examples show inclusion of the ECRTPAb1 inhibits the zone of proliferation around the implanted pellet.

As a final test to determine whether ECRTPAb1 functions to induce an angiostatic signal, we tested whether this antibody modified angiogenic responses to basic FGF in the mouse corneal pocket assay. Shown in FIG. 11, inclusion of ECRTPAb1, but not a control IgG, in the implanted slow release hydron pellet inhibited angiogenesis, scored by reducing the length of capillary sprouts as they approached the source of the angiogenic stimulus. This attenuation of capillary length, without effect on radial distribution of new vessles, suggests that pro-angiogenic basic FGF may diffuse more rapidly from the slow release pellet than ECRTPAb1, permitting brisk initiation of angiogenesis with subsequent attenuation.

EXAMPLE 3

Method of Screening for Endogenous Ligand of ECRTP/DEP-1 Receptor

Labelled ECRTP/DEP-1 Receptor is used to perform binding studies to identify cells with ECRTP/DEP-1 receptor ligands using Scatchard analysis; and to perform cross-linking studies which demonstrate the ECRTP/DEP-1 receptor ligand(s) on polyacrylamide gels. These initial characterization methods are use dot identify cells with high and low numbers of ECRTP/DEP-1 receptor ligand(s) for purification and isolation studies. Once a cell line with high levels of ECRTP/DEP-1 receptor ligand has been identified, then the protein is purified by the following approaches:

Approach A: Biochemical Purification

A cell line which expresses high levels of ECRTP/DEP-1 receptor ligand is lysed and the protein from lysates or membrane preparations is purified by gel filtration followed by purification of the ligand with a column containing the ECRTP/DEP-1 receptor bound to a solid phase such as sepharose. The purified ligand protein can then be microsequenced and the gene cloned using degenerate oligonucleotides derived form the protein sequence.

Approach B: cDNA Library Purification

The ECRTP/DEP-1 receptor is radiolabeled with $^{125}$I and then used to screen cell lines or tissues by Scratchard analysis for specific binding of ligand. Once such ligand binding is identified, a cDNA library is constructed from that tissue or cell line and transfected into a cell line that does not exhibit specific binding. These transfected cells are then screened for newly acquired specific binding which indicates they have been transfected with a construct containing the gene for the ECRTP/DEP-1 receptor ligand. Plasmid DNA from positive clones is then isolated and sequenced for identification. A single construct is then transfected back into the null cells to verify that binding between ligand and receptor is mediated by the transfected gene. Kluzen et al. *Proc Natl Acad Sci USA* 89:4618–4622 (1992).

Alternatively, chimeric ECRTP/DEP-1 receptor and immunoglobulin Fc molecules are constructed. LaRochelle et al., *J Cell Biol* 129:357–366 (1995). The chimeric molecules can then be used to screen for binding to ECRTP/DEP-1 receptor ligand on whole cells via flow cytometry. Alternatively, due to the presence of the immunoglobulin component of the molecule, cell lysates are screened by immunoblotting or by immunoprecipatiaion of metabolically labeled cells. This technique can identify ECRTP/DEP-1 receptor binding proteins by a variety of different methods. Peptide digests of the identified proteins are then generated so that peptides can be sequenced and the whole molecule cloned by the degenerative oligonucleotide approach.

REFERENCES

The references listed below as well as all references cited in the specification are incorporated herein by reference to the extent that they supplement, explain, provide a background for or teach methodology, techniques and/or compositions employed herein.

Ades et al., *J Invest Dermatol* 99:683–690 (1992).
Augenlicht and Baserga, *Exp Cell Res* 89:255–262 (1974).
Ausprunk et al., *Am J Pathol*, 79:597618 (1975).
Batt et al., *J Biol Chem* 273:3408–3414 (1998).
Bauer et al., *J Cell Physiol* 153:437–449 (1992).
Beekhuizen, H. and van Furth, R. *J Vascular Res* 31:230–239 (1994).
Bittner et al., *Methods in Enzymol* 153:516–544 (1987).
Bodanszky, et al., "Peptide Synthesis", John Wiley & Sons, Second Edition, (1976).
Borges et al., *Circulation Research* 79:570–580 (1996).
Cheresh et al., *J Biol Chem*, 262:17703–17711 (1987).
Choime et al., *J Biol Chem* 270:21144–21150 (1995).
Coomber, B. L. *J Cell Biochem* 52:289–296 (1993).
Daniel et al., *Kidney Int* 50:S-73-S-81 (1996).
de la Fuente-Garcia et al., *Blood* 91:2800–2809 (1998).
Desai et al., *Cell* 84:599–609 (1996).
Dilman et al., *Antibody Immunocon Radiopharm* 1:65–77 (1988).
Dulbecco et al., *Virol* 8:396 (1959).
Eijgenraam, F., *Science* 261:883–884 (1993).
Engerman et al., *Laboratory Investigation* 17:738–744 (1967).
EP 44167
Fields et al., *Int. J. Peptide Protein Res* 35:161–214 (1990).
Flickinger & Trost, *Eu. J. Cancer* 12(2):159–60 (1976).
Ghose et al., *CRC Critical Reviews in Therapeutic Drug Carrier Systems* 3:262–359 (1987).
Ghose et al., *Meth. Enzymology* 93:280–333 (1983).
Gumkowski et al., *Blood Vessels* 24:11–23 (1987).
Hailing et al., *Nucl Acids Res* 13:8019–8033 (1985).
Honda et al., *Blood* 84:4186–4194 (1994).
Huse et al., *Science* 246:1275–1281 (1989).
Hyink et al., *Am J Physiol* 270:F886–F899 (1996).
Inouye et al., *Nucleic Acids Res* 13:3101–3109 (1985).
Keane et al., *Cancer Research* 56:4236–4243 (1996).
Kimura et al., *Immunogenetics* 11:373–381 (1980).
Kitamoto et al., *J Clin Invest* 99:2351–2357 (1997).
Kluzen et al. *Proc Natl Acad Sci USA* 89:4618–4622 (1992).
Knowles & Thorpe, *Anal. Biochem* 120:440–443 (1987).
Koenig et al., *J Clin Immunol* 13:204–211 (1993).
Kohler and Milstein, *Nature* 256:495–497 (1975).
Kumet et al., *J Biol Chem* 271:30916–30921 (1996).
Lamb et al., *Eur Jrnl Biochem* 148:265–270 (1985).
Lampugnani et al., *J Cell Biol* 129:203–217 (1995).
LaRochelle et al., *J Cell Biol* 129:357–366 (1995).
Leveen et al., *Genes Dev* 8:1875–1887 (1994).
Logan et al., *Proc Natl Acad Sci USA* 81:3655–3659 (1984).
Lord et al., *In Genetically Engineered Toxins* (Ed. A. Frank, M. Dekker Publ., p. 183)(1992)
Lowy et al., *Cell* 22:817 (1980).
Martin et al., In Vitro *Cell Dev Biol* 33:261–269 (1997).
McOmie, J. F. W., "Protective Groups in Organic Chemistry", Plenum Press, New York, (1973).
Meienhofer, J., "Hormonal Proteins and Peptides", Vol. 2, p. 46, Academic Press (New York) (1983).
Merrifield, *Adv Enzymol*, 32:221–96 (1969).
More et al., *J Patho* 172:287–292 (1994).
Mulligan et al., *Proc Natl Acad Sci USA* 78:2072 (1981).
O'Hare et al., *FEBS Lett* 210:731 (1987).
Ogata et al., *J Biol Chem* 256:20678–20685 (1990).
Ossonski et al., *Cancer Res* 40:2300–2309 (1980)
Ostman et al., *Proc Natl Acad Sci USA* 91:9680–9684 (1994).
Pallen, C. J. and Tong, P. H. *Proc Natl Acad Sci USA* 88:6996–7000 (1991).
Palou et al., *Immunol Lett* 57:101–103 (1997).
Pietersz et al., *Antibody, Immunoconj Radiopharm* 1:79–103 (1988).
*Remington's Pharmaceutical Sciences*, 16th Ed. Mack Publishing Company, (1980)
Rijksen et al., *J Cell Physiol* 154:393–401 (1993).
Robert et al., *Am J Physiol* 271:F744–F753 (1996).
Robert et al., *Am J Physiol* 275:F164–F172 (1998).
Ruther et al., *EMBO J* 2:1791 (1983).
Sastry, et al., *Proc Natl Acad Sci USA* 86:5728–5732 (1989).
Schoecklmann et al., *J Am Soc Nephrol* 5:730 (1994) (abstract).
Scholz et al., *Cell Tissue Res* 290:623–631 (1997).
Schroder et al., "The Peptides", Vol. 1, Academic Press (New York) (1965).
Smith et al., *J Virol* 46:584 (1983).
Soriano, P., *Genes Dev* 8:1888–1896 (1994).
Stein et al., *J Biol Chem* 271:23588–23593 (1996)
Stein et al., *Genes Dev* 12:667–678 (1998).
Steward et al., "Solid Phase Peptide Synthesis", W.H. Freeman Co., San Francisco, (1969).
Szybalska et al., *Proc Natl Acad Sci USA* 48:2026 (1962).
Takahashi et al., *Kidney Int* 53:826–835 (1998).
Thomas et al., *J Biol Chem* 269:19953–19962 (1994).
Thorpe et al., *Cancer Res* 47:5924–5931 (1987).
Tsiotra et al., *J Biol Chem* 271:29216–29222 (1996).
U.S. Pat. No. 4,244,946
U.S. Pat. No. 4,215,051
U.S. Pat. No. 4,340,535
U.S. Pat. No. 4,472,509
U.S. Pat. No. 5,660,827
U.S. Pat. No. 5,733,876
U.S. Pat. No. 5,753,230
U.S. Pat. No. 5,762,918
U.S. Pat. No. 5,766,591
U.S. Pat. No. 5,776,427
Vaickus et al., *Cancer Invest* 9:195–209 (1991).
Van Heeke et al., *J Biol Chem* 264:5503–5509 (1989).
Vogel & Muller-Eberhard, *Anal. Biochem* 118(2):262–268 (1981).
Wallner et al., *Microsc Res Tech* 39:261–284 (1997).
Wang, Y. and Pallen, C. J., *J Biol Chem* 267:16696–16702 (1992).
Weiss, A. and Schiessinger, J., *Cell* 94:277–280 (1998).
Wigler et al., *Cell* 11:223 (1977).
Zimmer et al., *Peptides* (1992) pp. 393–394, ESCOM Science Publishers, B.V., (1993).
Zola, *Monoclonal Antibodies: a Manual of Techniques*, CRC Press, Inc. (1987).

What is claimed is:

1. A method of modulating angiogenesis in a vertebrate subject, the method comprising administering to the vertebrate subject an ECRTP/DEP-1 receptor activity-modulating amount of a composition, whereby an ECRTP/DEP-1 receptor within the vertebrate subject is contacted by the composition; and modulating angiogenesis through the contacting of the ECRTP/DEP-1 receptor with the composition.

2. The method of claim 1, wherein the composition comprises a monoclonal antibody which selectively binds the ECRTP/DEP-1 receptor.

3. The method of claim 2, wherein the monoclonal antibody is monoclonal antibody ECRTPAb-1, having a molecular weight of about 150 kDa and which selectively binds to an ectodomain of the ECRTP/DEP-1 receptor.

4. The method of claim 3, wherein the ECRTP/DEP-1 receptor activity-modulating amount of the monoclonal antibody ranges from about 0.1 to about 300 milligrams per kilogram body weight of the vertebrate subject.

5. The method of claim 4, wherein the ECRTP/DEP-1 receptor activity-modulating amount of the monoclonal antibody ranges from about 0.2 to about 200 milligrams per kilogram body weight of the vertebrate subject.

6. The method of claim 5, wherein the ECRTP/DEP-1 receptor activity-modulating amount of the monoclonal antibody ranges from about 0.5 to about 20 milligrams per kilogram body weight of the vertebrate subject.

7. The method of claim 3, wherein the monoclonal antibody is further characterized as having the immunoreaction characteristics of a monoclonal antibody produced by a hybridoma cell line having ATCC accession number HB12570.

8. The method of claim 7, where the monoclonal antibody is monoclonal antibody produced by a hybridoma cell line having ATCC accession number HB12570.

9. The method of claim 2, wherein the antibody is humanized.

10. The method of claim 9, wherein the humanized antibody is humanized monoclonal antibody ECRTPAb-1, having a molecular weight of about 150 kDa and which preferentially binds to an ectodomain of the ECRTP/DEP-1 receptor.

11. The method of claim 10, wherein the humanized antibody is further characterized as having the immunoreaction characteristics of a monoclonal antibody produced by a hybridoma cell line having ATCC accession number HB12570.

12. The method of claim 11, where the monoclonal antibody is monoclonal antibody produced by a hybridoma cell line having ATCC accession number HB12570.

13. The method of claim 1, wherein the administering is selected for the group consisting of intravenous administration, intrasynovial administration, transdermal administration, intramuscular administration, subcutaneous administration and oral administration.

14. The methods of claim 1, wherein the administering is conducted in conjunction with chemotherapy.

15. The method of claim 1, wherein the vertebrate subject is a mammal.

16. The method of claim 15, wherein the mammal is a human.

17. The method of claim 1, wherein said angiogenesis comprises angiogenesis in a solid tumor in a patient, and wherein an ECRTP/DEP-1 receptor expressed on the surface of vascular endothelial cells involved in the angiogenesis is contacted by the composition resulting in inhibition in the blood supply to tissue of the solid tumor.

18. The methods of claim 17, wherein the administering is conducted in conjunction with chemotherapy.

19. The method of claim 17, wherein the patient is a human.

20. The method of claim 1, wherein the angiogenesis comprises angiogenesis in an inflamed tissue of a patient and wherein an ECRTP/DEP-1 receptor expressed on the surface of vascular endothelial cells involved in the angiogenesis in the inflamed tissue is contacted by the modulator resulting in inhibition in the blood supply to the inflamed tissue.

21. The method of claim 20, wherein the patient is a human.

22. A method of modulating angiogenesis in a vertebrate subject, the method comprising administering to the vertebrate subject an ECRTP/DEP-1 receptor activity inhibiting amount of an antibody, wherein the antibody selectively binds the ECRTP/DEP-1 receptor, whereby an ECRTP/DEP-1 receptor within the vertebrate subject is contacted by the antibody; and inhibiting angiogenesis through the contacting of the ECRTP/DEP-1 receptor with the antibody.

* * * * *